United States Patent
Koltowski et al.

(10) Patent No.: US 11,540,726 B2
(45) Date of Patent: Jan. 3, 2023

(54) PORTABLE SPIROMETER

(71) Applicant: HEALTHUP SP. Z O.O., Warsaw (PL)

(72) Inventors: Lukasz Koltowski, Warsaw (PL); Piotr Bajtala, Warsaw (PL)

(73) Assignee: HEALTHUP SPÓLKA AKCYJNA, Warsaw (PL)

( * ) Notice: Subject to any disclaimer, the term of this patent is extended or adjusted under 35 U.S.C. 154(b) by 661 days.

(21) Appl. No.: 16/343,327

(22) PCT Filed: Oct. 19, 2017

(86) PCT No.: PCT/EP2017/076710
§ 371 (c)(1),
(2) Date: Apr. 18, 2019

(87) PCT Pub. No.: WO2018/073343
PCT Pub. Date: Apr. 26, 2018

(65) Prior Publication Data
US 2019/0254534 A1 Aug. 22, 2019

(30) Foreign Application Priority Data

Oct. 20, 2016 (PL) ........................................ 419194
Nov. 9, 2016 (EP) .................................... 16197970
Aug. 18, 2017 (EP) .................................... 17461593

(51) Int. Cl.
*A61B 5/0205* (2006.01)
*A61B 5/087* (2006.01)
(Continued)

(52) U.S. Cl.
CPC .......... *A61B 5/0205* (2013.01); *A61B 5/0002* (2013.01); *A61B 5/087* (2013.01);
(Continued)

(58) Field of Classification Search
CPC ................................. A61B 5/087; G01F 1/44
See application file for complete search history.

(56) References Cited

U.S. PATENT DOCUMENTS

| 5,137,026 A | 8/1992 | Waterson et al. |
| 6,032,527 A | 3/2000 | Genova et al. |

(Continued)

FOREIGN PATENT DOCUMENTS

| CN | 104519795 A | 4/2015 |
| CN | 205359478 U | 7/2016 |

(Continued)

OTHER PUBLICATIONS

"Standardization of Spirometry, 1994 Update. American Thoracic Society," American Journal of Respiratory and Critical Care Medicine, 152(3), pp. 1107-1136,.
(Continued)

*Primary Examiner* — Gary Jackson
*Assistant Examiner* — Zahed Kabir
(74) *Attorney, Agent, or Firm* — Hoxie & Associates LLC

(57) ABSTRACT

The invention relates to a spirometer (1) comprising a MEMS-based thermal fluid flow sensor (13, 13.1, 13.2) for generating a signal in response to a fluid flow generated during inhalation or exhalation; and a microcontroller (14) for calculating the fluid flow from the signal generated by the flow sensor (13, 13.1, 13.2). The spirometer (1) may be connected to other devices, such as a smartphone or a personal computer or any other computing unit which is adapted to collect, store, analyse, exchange and/or display data. The invention further describes the use of the spirometer (1) in measuring a user's lung performance and/or monitoring it over time. Furthermore, the spirometer (1) may be provided in a system together with an air quality measurement device for determining the air quality at a
(Continued)

location of interest; and a computing unit for collecting, analysing and correlating the user's lung performance data obtained from the spirometer (1) with the air quality data, and optionally geolocalisation data of said location.

52 Claims, 7 Drawing Sheets

(51) Int. Cl.
*A61B 5/1455* (2006.01)
*A61B 5/00* (2006.01)
*G01F 1/68* (2006.01)
*G01F 1/44* (2006.01)
*A61B 5/024* (2006.01)

(52) U.S. Cl.
CPC ............ *A61B 5/14552* (2013.01); *G01F 1/44* (2013.01); *G01F 1/68* (2013.01); *A61B 5/02438* (2013.01); *A61B 2560/0214* (2013.01); *A61B 2560/0252* (2013.01); *A61B 2560/0257* (2013.01); *A61B 2562/028* (2013.01); *A61B 2562/029* (2013.01); *A61B 2562/0271* (2013.01)

(56) References Cited

U.S. PATENT DOCUMENTS

| | | | |
|---|---|---|---|
| 6,322,519 | B1 | 11/2001 | Moulin |
| 6,795,752 | B1 | 9/2004 | Zhao et al. |
| 9,861,229 | B2 | 1/2018 | Jones et al. |
| 2002/0026937 | A1 | 3/2002 | Mault |
| 2004/0039295 | A1 | 2/2004 | Olbrich et al. |
| 2004/0186390 | A1 | 9/2004 | Ross et al. |
| 2004/0249300 | A1* | 12/2004 | Miller .................. A61M 16/10 600/532 |
| 2009/0139347 | A1* | 6/2009 | Speldrich .................. G01F 5/00 73/861.63 |
| 2010/0305466 | A1 | 12/2010 | Corn |
| 2011/0066042 | A1 | 3/2011 | Pandia et al. |
| 2012/0136271 | A1* | 5/2012 | Shavit .................... A61B 5/087 600/538 |
| 2012/0186338 | A1* | 7/2012 | Bonnat ...................... G01P 5/04 73/272 R |
| 2013/0167630 | A1 | 7/2013 | Ueda et al. |
| 2013/0172773 | A1 | 7/2013 | Halwani et al. |
| 2013/0217979 | A1 | 8/2013 | Blackadar et al. |
| 2013/0267864 | A1 | 10/2013 | Addington et al. |
| 2013/0317379 | A1 | 11/2013 | Brimer et al. |
| 2014/0379292 | A1 | 12/2014 | Ara et al. |
| 2015/0164373 | A1* | 6/2015 | Davis ................... A61B 5/0871 600/532 |
| 2016/0120441 | A1 | 5/2016 | Zhu |
| 2016/0242701 | A1 | 8/2016 | Gonnen et al. |
| 2016/0256073 | A1* | 9/2016 | Grudin .................. A61B 5/085 |
| 2017/0266399 | A1* | 9/2017 | Campana ............ A61M 16/107 |
| 2017/0270260 | A1* | 9/2017 | Shetty ..................... A61B 5/087 |
| 2018/0008790 | A1 | 1/2018 | Costella et al. |
| 2018/0066970 | A1* | 3/2018 | Pern ........................ G01F 1/684 |
| 2019/0385727 | A1* | 12/2019 | Manice ............... A61M 15/008 |

FOREIGN PATENT DOCUMENTS

| | | |
|---|---|---|
| EP | 0552916 | 7/1993 |
| JP | H0428350 | 1/1992 |
| JP | 1998-503097 A | 3/1998 |
| JP | 2004-514140 | 5/2004 |
| JP | 2010-528684 A | 8/2010 |
| JP | 2012-026930 | 2/2012 |
| JP | 2013-158593 | 8/2013 |
| RU | 2396903 | 8/2010 |
| RU | 2449813 | 5/2012 |
| WO | WO 1996/02187 A1 | 2/1996 |
| WO | WO 2002/041007 A2 | 5/2002 |
| WO | WO 2005/096932 | 10/2005 |
| WO | WO 2008/144433 A1 | 11/2008 |
| WO | WO 2009/067549 | 5/2009 |
| WO | WO 2012/014632 A1 | 2/2012 |
| WO | WO 2012/169003 A1 | 12/2012 |
| WO | WO 2013/043847 A1 | 3/2013 |
| WO | WO 2013/188458 A2 | 12/2013 |
| WO | WO 2016/041576 A1 | 3/2016 |

OTHER PUBLICATIONS

Written Opinion of the International Searching Authority for International Application No. PCT/EP2017/076710 dated May 14, 2018, 8 pages.

Written Opinion of the International Searching Authority for International Application No. PCT/EP2019/060193 dated Jul. 26, 2019, 10 pages.

Miller, M.R., et al., "Standardisation of spirometry," European Respiratory Journal, 2005, 26(2), pp. 319-338.

Quanjer, P.H., et al., "Peak expiratory flow: conclusions and recommendations of a Working Party of the European Respiratory Society," European Respiratory Journal, 1997, 10(24), pp. 2s-8s.

Written Opinion of the International Searching Authority for International Application No. PCT/EP2017/076710 dated May 14, 2018, 5 pages.

* cited by examiner

PORTABLE SPIROMETER

CROSS-REFERENCE TO RELATED APPLICATIONS

This application is a National Stage Entry under 35 U.S.C. § 371 of International Application No. PCT/EP2017/076710, filed Oct. 19, 2017, which claims priority from European Application Number 17461593.0, filed Aug. 18, 2017, which claims priority from European Application Number 16197970.3, filed Nov. 9, 2016, and which claims priority from Polish Application Number P.419194, filed Oct. 20, 2016, the contents of each of which are incorporated by reference in their entirety.

BACKGROUND OF THE INVENTION

The invention is related to a portable spirometry device, or spirometer, as well as a method for determining lung function parameters using said device.

Spirometry is one of the most common tests used for determining, or evaluating, pulmonary function in terms of lung function parameters relating to the amount (volume) and/or speed (flow, or flow rate) of air that can be inhaled and exhaled, either forcedly or under normal breathing. The primary signals measured in spirometry may be volume and/or flow. Results are provided both as raw data (litres, litres per second) and as percent predicted, i.e. in relation to predicted values for patients of similar parameters such as height, age, sex, weight and sometimes ethnicity. Since multiple publications of predicted values are available, the interpretation of the results may vary slightly, but generally speaking, results close to 100% predicted are the most normal, and results ≥80% are usually also considered normal. Commonly, the results are further displayed as graphs, so called spirograms or pneumotachographs, showing a volume-time curve (volume in litres on the Y-axis and time in seconds on the X-axis) and/or a flow-volume loop (depicting the rate of airflow on the Y-axis and the total volume inhaled or exhaled on the X-axis).

Spirometry is an important tool in the assessment of various obstructive or restrictive lung conditions such as asthma, chronic obstructive pulmonary disease (COPD), bronchitis, emphysema, pulmonary fibrosis (PF), and also cystic fibrosis (CF), because the tests performed with the so-called spirometer (i.e. a device, or apparatus, for measuring ventilation, the movement of air into and out of the lungs) are able to identify abnormal ventilation patterns, namely obstructive and restrictive patterns.

Lung function parameters that can be determined using spirometry and/or a spirometer include e.g.: vital capacity (VC; volume exhaled after deepest inhalation); forced vital capacity (FVC; determination of the vital capacity from a maximally forced expiratory effort); slow vital capacity (SVC); forced expiratory flow (FEF), peak expiratory flow (PEF; highest forced expiratory flow, measured with a peak flow meter); forced expiratory volume (FEV$_X$; volume of air exhaled under forced conditions in the first X seconds; e.g. FEV$_1$=volume force-exhaled after 1 second); forced expiratory time (FET), inspiratory vital capacity (IVC; maximum volume inhaled after maximum expiration); forced inspiratory vital capacity (FIVC); residual volume (RV; volume of air remaining in the lungs after maximum exhalation; sometimes expressed in percent based on total lung capacity); total lung capacity (TLC; volume in lungs after maximum inhalation; sum of VC and RV); tidal volume (TV; volume of air moved into or out of the lungs during quiet breathing); inspiratory or expiratory reserve volume (IRV and ERV; maximal volume that can be inhaled or respectively exhaled from the end-inspiratory level or respectively end-expiratory level); inspiratory capacity (IC; sum of IRV and TV); functional residual capacity (FRC; volume in the lungs at the end-expiratory position); extrapolated volume (EVOL), estimated lung age (ELA); maximal voluntary ventilation (MVV; also called maximum breathing capacity); and others.

As mentioned, the test procedures are performed using a spirometer. Various types of these devices are known, from simple mechanically operating to fully electronic ones; said devices using a number of different measurement principles such as water gauges, 'windmill'-type rotors (also called turbines) or pressure transducers. Most conventional spirometers evaluate the fluid flow by measuring either a pressure difference before and after a membrane, capillaries or other forms of flow restriction with a known resistance (e.g. using a differential pressure sensor), or by the rotations of a turbine. In the past, efforts increased to render the devices portable and/or handheld, in order to obtain a more detailed and concise monitoring of e.g. therapy efficacy by allowing the patients, or users, to perform spirometry measurements by themselves; thereby obviating the need to visit a doctor's office or a hospital. Some of these portable devices are even aimed at being connectable to e.g. a patient's smartphone.

For instance, the Vitalograph's asma-1 device is a small, handheld, AAA-battery-powered device to measure and store PEF and FEV$_1$ values. The device is equipped with a rotatable turbine and disposable mouthpieces and can be connected via USB or Bluetooth to a mobile phone, PDA, PC or home hub. Unfortunately, the device can store only a limited number of measurements (up to 600) and no parameters other than PEF and FEV$_1$ can be measured. In other words, no full spirometry as defined by the spirometry standards of the American Thoracic Society (ATS) and the European Respiratory Society can be performed by the device; see "Standardisation of spirometry"; Eur Respir J 2005; 26: 319-338 (for instance, these standards define 24 ATS waveforms that the spirometer must correctly identify, some of these generated at higher temperature of 37° C. and high humidity, and additionally, the total resistance to airflow at 0-14.0 L/s must be <0.15 kPa/(L/s)).

Baltimore based company Respi is working on an iPhone® spirometer and a respective respiratory data platform. Respi's prototypical 3D printed spirometer aims at using the smartphone (Apple's Lightning Connector for iPhone® 5s) as a power source and the smartphone's internal sensors to ensure proper body posture during the measurement. The device is equipped with a rotating wing and a laser sensor taking several thousand measurements per second. The collected data are said to be adjusted based on environmental conditions such as pressure and temperature, and any gathered information on a cloud which allows constant patient monitoring, individual spirometry assessment, personalized real-time consultation and big population analytics. Disposable mouthpieces from MIR (Medical International Research) are used to ensure hygiene. While the spirometer is capable of full spirometry (e.g. not just peak flow measurements), it is also associated with various drawbacks; e.g. the smartphone application (or 'app') is currently missing the option to coach a patient through a breathing manoeuver for 6 seconds. Furthermore, dedicated adapters and/or wireless communication mechanisms would be required to work with other types of smartphones than the iPhone® (Respi suggests Bluetooth 4.0).

Introduced in 2012, SpiroSmart is a low-cost mobile phone application that performs spirometry (namely $FEV_1$, FVC, PEF, and $FEV_1\%$) using the built-in microphone in the smartphone (iPhone®). The app is intended for non-chronic disease management, and monitoring air quality effects and/or allergic reactions. The app records the user's exhalation and uploads the audio data generated with the microphone to a server. The server then calculates the expiratory flow rate using a physiological model of the vocal tract and a model of the reverberation of sound around the user's head, and final results are then sent back to the smartphone app. However, the system and app are associated with a number of disadvantages. According to the inventors, usability and training challenges exist and patients with severely low lung function may not generate any sound. Algorithms created from audio data collected on a specific smartphone model may not be generalisable to other models or brands. Further, the user needs to ensure that he always holds the smartphone at the same position (e.g. an arms length from the mouth) and at the correct angle; and that he opens his mouth wide enough. SpiroSmart—same as a majority of spirometry tests relying on sound signals—can only be used in quiet settings, and in contrast to full spirometry as performed e.g. in hospital settings, the inhalation which is typically (almost) inaudible would not be recorded by the smartphone. And currently the smartphone app cannot calculate all features in real time; especially the flow-volume loops requiring extensive computation, such that the analysis is done in the cloud (i.e. storage of digital data on one or multiple physical servers, typically owned and managed by a hosting company).

Alternatively to SpiroSmart, a call-in-service (SpiroCall) may be used by users who do not own a smartphone. In that case, the standard telephony voice channel is employed to transmit the sound of the spirometry effort. The tests can be performed either with or without the use of a simple 3D-printed SpiroCall whistle which generates vortices as the user exhales through it, changing its resonating pitch in proportion to the flow rate. SpiroCall combines multiple regression algorithms to provide reliable lung function estimates despite the degraded audio quality over a voice communication channel. The server then computes the lung function parameters and the user receives a response via a text message on their phones.

A similar acoustics based and smart-phone connectable device is AirSonea®'s portable 'digital stethoscope' and its related smartphone app which records breath sounds to detect and measure wheeze, a typical sound resulting from a narrowing of the airways and one of the primary signs of asthma. The AirSonea® sensor is held at the trachea (windpipe) during 30 seconds of normal breathing. The app then records and analyses the breathing sounds and returns a WheezeRATE™, a measurement of the extent of wheezing over the duration. The WheezeRATE™ history is stored in the smartphone and synced to the Cloud for review and sharing with e.g. healthcare professionals However, wheeze is not well validated clinically for monitoring of asthma treatment (lack of clinical guidelines in this field) and the device is not capable of measuring spirometric parameters.

Medical International Research's (MIR) offers a broad range of devices for measurements of respiratory parameters, some of them portable and some connectable to mobile phones. For instance, the Smart One® device is a portable turbine flowmeter, optionally using MIR's customary disposable FlowMIR® turbine and cardboard mouth piece. The device can be connected via Bluetooth to a smartphone on which the respective Smart One® app (available for iOS and Android) and the measured respiratory data are stored. The device is capable of determining e.g. PEF and $FEV_1$; however, no full spirometry can be performed with the device.

MIR's Spirodoc® and Spirobank® II Smart devices are portable, pocket-sized, standalone (i.e. requiring no computer) turbine flowmeter devices capable of performing full spirometry and storing up to 10.000 spirometry tests. The Spirodoc® device comprises an approximately palm-sized main body with an LCD touchscreen display, an attachable flowmeter head housing a bi-directional digital turbine (e.g. the disposable FlowMIR® turbine), and a temperature sensor for BTPS conversion of FVC measurements (i.e. vital capacity at maximally forced expiratory effort, expressed in litres at body temperature and ambientpressure saturated with water vapour). The Spirobank® II Smart device differs mainly in that a keyboard is used instead of Spirodoc®'s touchscreen and in that the flowmeter head is permanently fixed. Alternatively to the keyboard, the Spirobank® II Smart device may also be operated via a tablet computer (iPad™). A smartphone connectivity is not provided, though.

Both devices may optionally further comprise a fingertip pulse oximeter that can be attached via cable to the main body. A built-in three-axis movement sensor is provided in the devices in order to correlate the oxygen saturation level (% SpO2) measured with the fingertip oximeter to the user's physical activity. Data transmission, e.g. to a personal computer (PC) running the related WinspiroPRO® software—or for the Spirobank® Smart an iPad/iPad mini running the iOS-based MIR Spiro® app—may be achieved via Bluetooth or USB connection. Only when connected to a PC or iPad, the respective software allows for real time spirometry and oximetry tests; i.e. real time curve display. Unfortunately, this need of e.g. a tablet computer or the like increases the costs for these devices.

A further portable, pocket size homecare spirometer in the product range of MIR is the Spirotel® which uses an attachable, reusable bi-directional digital turbine and a small touchscreen in a main-body that is connectable to a personal computer (PC) via a USB-cable or Bluetooth; a software application (WinspiroPro Home Care) then extracts the data and sends it to a server. Same as with the Spirodoc® and Spirobank® II Smart devices, the Spirotel® may optionally further comprise a fingertip pulse oximeter that can be attached via cable to the main body, and a built-in three axis movement sensor to correlate the measured oxygen saturation level (% SpO2) to the user's physical activity. While being portable itself, the Spirotel® device cannot be used as a standalone and is not connectable to smart phones, but requires the use of a PC instead.

One common disadvantage of most of the above listed devices is the use of movable parts, namely the turbines or rotating wings, to measure gas flow. This necessitates regular external calibrations, e.g. annually or biannually. Furthermore, a majority also lacks the option to measure spirometric parameters such as $FEV_6$, FRC, SVC, MVV or ERV.

A portable, battery operated device using a gas flow sensor without movable parts is the SpiroTube mobile edition by Thor Laboratories, a pulmonary function diagnostics and monitoring device with Bluetooth or USB connection to a PC (storing the ThorSoft pulmonary diagnostics PC software). Bluetooth and also WIFI connection is available as an option to connect the SpiroTube to iPad/iPhone, Android smartphones, PDA devices as well as any JAVA-ready mobile device. The SpiroTube uses the proprietary IDEGEN™ multipath measurement principle wherein the flow volume measurement depends on the quantity and energy of gas molecules, measured using ultrasound and the Doppler Effect. The inner surface of the flow tube is continuous and free of any obstacles such that it can be disinfected easily.

A further device without movable parts is the WING device by US-based Sparo Labs which can be cable-connected to a smartphone via the headphone jack and which measures PEF (peak expiratory flow) and $FEV_1$ (volume force-exhaled after 1 second). Measured data are synced to a 'cloud' in encrypted form and can be analysed using a dedicated smartphone application. Unfortunately, no parameters other than PEF and $FEV_1$ can be measured (e.g. no forced vital capacity (FVC), forced expiratory flow at 25%-75% of FVC (FEF25-75), etc.). In other words, no full spirometry as defined by the spirometry standards of the American Thoracic Society (ATS) and the European Respiratory Society can be performed; similar to e.g. the asma-1 device described above. Also, the WING runs on the phone's battery (via the headphone jack), such that it is at risk to not measure data properly if the phone battery is low.

Alternatively, acceleration sensors (also called accelerometers or gyro-sensors) such as MEMS based thermal fluid flow sensors (MEMS; microelectromechanical systems) have also been suggested in the prior art for flow measurements in medical devices including ventilators, sleep apnoea devices, spirometers, etc.; for instance, by MEMSIC, one of the producers of these type of sensors. These MEMS based thermal fluid flow sensors use temperature sensors, such as thermocouples, and gas molecules heated via a resistive heating element. When subjected to acceleration, the less dense molecules in the heated gas move in the direction of acceleration and the cool and denser molecules move in the opposite direction, creating an acceleration proportional temperature difference measured by the temperature sensors. However, to the best of the inventor's knowledge, this conceptual idea of employing MEMS based thermal fluid flow sensors for flow measurements in medical devices has never been translated into an existing, operable, functional spirometer before; i.e. up to the present invention, it was not clear whether the concept could actually be put into practice and how exactly accurate and reproducible, or precise, spirometric flow measurements could be achieved.

It is an object of the present invention to provide an improved portable spirometer which overcomes the draw backs of prior art devices; e.g. a device with higher measurement sensitivity that can be used without medically trained staff and which is capable of performing full spirometry, including measurements of main spirometry paramters such as $FEV_1$, FVC, PEF, and $FEV_1\%$ but also parameters such as $FEV_6$, FRC, SVC, MVV or ERV. This object is achieved by the subject matter of the present invention as set forth in the claims, namely by a portable spirometer employing MEMS based thermal fluid flow sensors as a measurement principle. It was further an object of the present invention to provide a portable spirometer with a MEMS based thermal fluid flow sensor, which is optimized with regard to the flow properties inside the device in order to enable accurate and reproducible, or precise, spirometric flow measurements.

SUMMARY OF THE INVENTION

In a first aspect, the invention provides a portable electronic spirometer comprising (a) a tubular mouthpiece and (b) a main body. The tubular mouthpiece comprises a proximal opening for insertion into the mouth of a user, a distal opening, and a main fluid channel extending between these two openings. The mouthpiece further comprises a first lateral opening and a second lateral opening positioned at a longitudinal distance to the first; as well as a flow restrictor positioned in the main fluid channel between the first and the second lateral opening. The main body comprises a first fluid opening connectible with the first lateral opening of the mouthpiece, a second fluid opening connectible with the second lateral opening of the mouthpiece, and a bypass fluid channel extending between the first and the second fluid opening. The main body further comprises a MEMS-based thermal fluid flow sensor positioned at the bypass fluid channel for generating a signal in response to the fluid flow in the bypass fluid channel; and a microcontroller connected with the fluid flow sensor for calculating the fluid flow from the signal generated by the flow sensor. One embodiment of this spirometer is depicted e.g. in FIG. 2.

The flow restrictor in this spirometer may exhibit a flow resistance, or impedance, in the range from about 0.01 to about 0.2 kPa/(L/s), preferably from about 0.01 to about 0.15 kPa/(L/s), and more preferably from about 0.01 to about 0.1 kPa/(L/s) at a fluid flow of 60 SLM to 900 SLM (or SLPM; standard liter per minute); and/or it may be adapted or configured such as to cause a fluid flow in the bypass fluid channel which is from about 1:10 to about 1:200 of the fluid flow in the main fluid channel, i.e. a the fluid flow in the bypass channel may range from about 0.3 SLM to about 90 SLM. The flow restrictor may be a perforated disk having a cross-sectional orientation with respect to the main fluid channel, e.g. a perforated disk exhibiting from about 1 to about 100 perforations, or from about 2 to about 100 perforations, or from about 4 to about 100 perforations, or from about 15 to about 100 perforations (optionally circular, elliptic or polygonal in shape, or shaped as sectors of a circle or oval), and/or exhibiting a total combined area of all perforations ranging from about 26% to about 96%, or from about 39% to about 96%, or from about 26% to about 72%, of the cross-sectional area of the main fluid channel at the position of the perforated disk. For instance, the flow restrictor may be a perforated disk with a total surface area of about 587 $mm^2$, comprising 55 perforations which are shaped as regular hexagons and exhibit a 'perforated surface area' of about 175 $mm^2$, or about 30% of the flow restrictor's total surface area; or the flow restrictor may be a perforated disk with a total surface area of about 587 $mm^2$, comprising 37 perforations of circular shape and a 'perforated surface area' of about 261 $mm^2$, or about 45% of the flow restrictor's total surface area.

The distance between said flow restrictor and the first lateral opening along the longitudinal axis of the main fluid channel of the spirometer may be from about 5 mm to about 15 mm, preferably about 10 mm, e.g. 10.0 mm; and the distance between the flow restrictor and the second lateral opening from about 25 mm to about 45 mm, preferably about 34 mm, e.g. 34.2 mm.

The MEMS-based thermal fluid flow sensor of the spirometer may be a bidirectional flow sensor, such as to allow e.g. for measurements during both inhalation and exhalation. The MEMS-based thermal fluid flow sensor may e.g. be a monolithic complementary metal-oxide-semiconductor (CMOS) flow sensor comprising a sensor chip, the chip comprising an encapsulated gas bubble, a microheater for heating the gas bubble, a first plurality of thermopiles located on a first side of the gas bubble, and a second plurality of thermopiles located on a second side of the gas bubble which is opposite to the first side. This type of flow sensor also acts as a temperature sensor for measuring the temperature of the breath at the same time.

The spirometer may further comprise an acceleration sensor which is different from the MEMS-based thermal fluid flow sensor, for instance a 3-axis sensor with a sensitivity (So) of at least 973 counts/g±5% for each of the three axes; typically, the sensitivity ranges between 973 and 1075 counts/g; e.g. 1024 counts/g. Such acceleration sensors e.g. allow for correcting the calculated fluid flow. For instance, the microcontroller of the spirometer may be programmed to calculate a corrected fluid flow from the signal generated by the flow sensor and from a signal generated by the acceleration sensor. Furthermore, this acceleration sensor may also be employed—similar to the MEMS-based thermal fluid flow sensor—for measuring the temperature of the breath.

The spirometer may further comprise a heart rate sensor, a blood oxygen saturation sensor, a temperature sensor for measuring the temperature of the environment, an atmospheric pressure sensor, and/or a moisture sensor. Each of these one or more sensors may be directly or indirectly connected with the microcontroller such that the microcontroller is capable of receiving a signal from each of the one or more sensors.

The spirometer may further comprise a communication means, preferably a wireless communication means, and more preferably a radio communication means.

Furthermore, the spirometer may exhibit a mean energy consumption of the device during its operation which is not higher than 90 mA in total, preferably not higher than about 50 mA.

In a second aspect, the invention provides a method for measuring a health parameter of a human subject selected from a forced vital capacity (FVC), a forced expiratory volume (FEV), a peak expiratory flow (PEF), a forced expiratory flow (FEF), a maximum voluntary ventilation (MVV), a mean expiratory flow, a slow vital capacity (SVC), a functional residual capacity (FRC), an expiratory reserve volume (ERV), a maximum speed of expiration, a forced inspiratory volume (FIV), a forced inspiratory vital capacity (FIVC), a peak inspiratory flow (PIF), or any combination of these, the method comprising a step of the human subject performing a breathing manoeuvre through the spirometer as described above.

In a third aspect, the invention provides a system comprising:
  the portable electronic spirometer (1) according to the first aspect of the invention, and
  a first air quality measurement device comprising communication means adapted for data exchange with the portable electronic spirometer (1) and/or with a separate computing unit, and equipped with one or more air quality sensors, prefereably selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors, for determining determine the air quality at the location of the first air quality measurement device, and optionally
  a separate computing unit adapted to collect and analyse at least the data obtained from the spirometer (1) according to the first aspect of the invention and from the first air quality measurement device.

Using said system, the method according to the second aspect of the invention may be complemented with additional data such as data related to the air quality (pollutants, ozone, pollen, etc.) and/or geolocation data, thereby allowing to compare and/or correlate the health parameter of the human subject (such as FVC, FEV, PEF, FIV, FIVC, PIF, etc., as described above) with these additional data.

In other words, a fourth aspect of the invention provides a method wherein one or more health parameters of a human subject selected from a forced vital capacity (FVC), a forced expiratory volume (FEV), a peak expiratory flow (PEF), a forced expiratory flow (FEF), a maximum voluntary ventilation (MVV), a mean expiratory flow, a slow vital capacity (SVC), a functional residual capacity (FRC), an expiratory reserve volume (ERV), a maximum speed of expiration, a forced inspiratory volume (FIV), a forced inspiratory vital capacity (FIVC), a peak inspiratory flow (PIF), or any combination of these, are measured by the human subject performing a breathing manoeuvre through the spirometer according to the first aspect of the invention; and wherein the one or more health parameters are compared and/or correlated with air quality data, and optionally geolocalisation data, derived from the system according to the third aspect of the invention.

Further objects, aspects, useful embodiments, applications, beneficial effects and advantages of the invention will become apparent on the basis of the detailed description, the examples and claims below.

OVERVIEW OF REFERENCE NUMBERS

| | |
|---|---|
| 1 | Spirometer |
| 2 | Tubular mouthpiece |
| 2.1 | Front end of mouthpiece |
| 3 | Proximal opening |
| 4 | Distal opening |
| 5 | Main fluid channel |
| 6 | First lateral opening |
| 7 | Second lateral opening |
| 8 | Flow restrictor |
| 8.1 | Perforated disk |
| 8.2 | Perforations |
| 8.3 | Rib(s) |
| 8.4 | Outer ring |
| 9 | Main body |
| 10 | First fluid opening |
| 11 | Second fluid opening |
| 12 | Bypass fluid channel |
| 13 | MEMS-based thermal fluid flow sensor |
| 13.1 | Bidirectional flow sensor |
| 13.2 | Monolithic CMOS flow sensor |
| 14 | Microcontroller |
| 15 | Acceleration sensor |
| 15.1 | 3-axis sensor |
| 16 | Heart rate sensor |
| 17 | Blood oxygen saturation sensor |
| 18 | Environmental temperature sensor |
| 19 | Atmospheric pressure sensor |
| 20 | Moisture sensor |
| 21 | Radio communication means |
| 21.1 | Bluetooth connectivity |
| 21.2 | NFC means |
| 21.3 | WLAN means |
| 22 | Cable communication means |
| 22.1 | USB communication means |
| 23 | Optical signalling means |
| 23.1 | Signalling LEDs |
| 24 | Acoustical signalling means |
| 25 | ON/OFF-button |
| 26 | Battery |
| 27 | Main board |
| 28 | Breath temperature sensor |

BRIEF DESCRIPTION OF THE FIGURES

FIG. 3A, here 55), or circular perforations (8.2; FIG. 3B, here 37), or perforations shaped as sectors of a circle or oval (8.2, FIG. 3C, here 6) dissected by straight ribs (8.3), or irregularly shaped perforations (8.2, FIG. 3D).

Figure 3A:
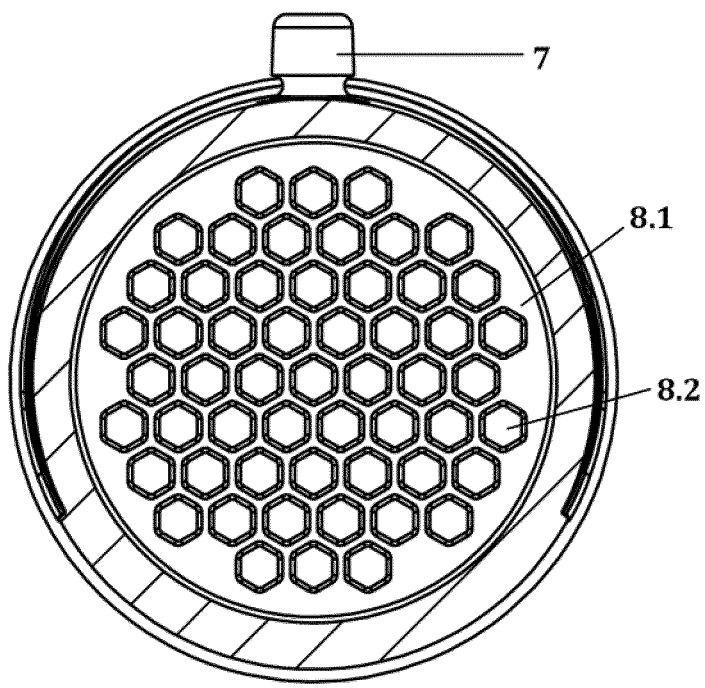
FIGS. 3A, 3B, 3C and 3D show crosssections of four embodiments of the spirometer (1) at the position of the flow restrictor (8), more specifically at the position of a perforated disk (8.1) as employed in specific embodiments of the spirometer (1), with either regular hexagonal perforations (8.2.
Figure 3B:
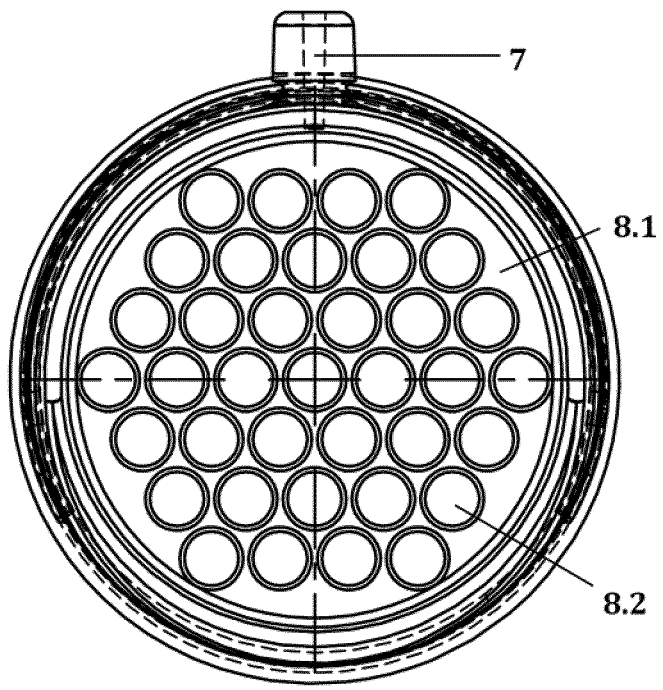
Figure 3C:
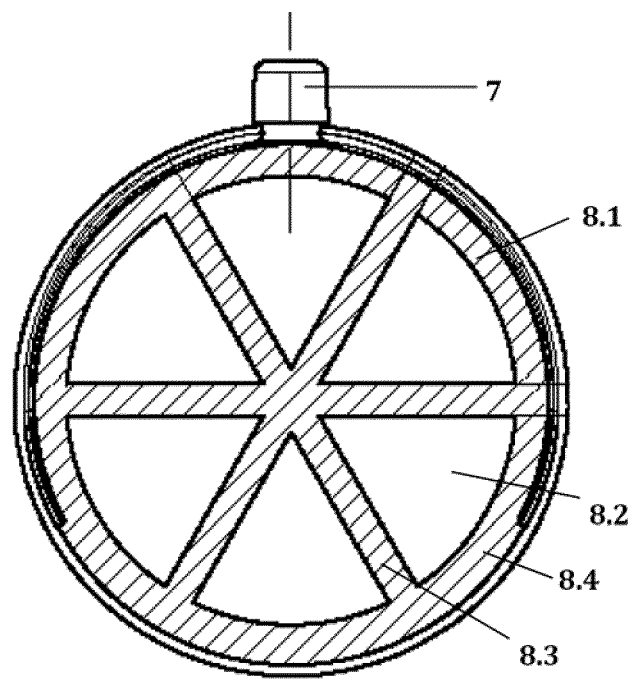

As can be seen in FIG. 3C, the depicted exemplary perforated disk (8.1) comprises an outer ring (8.4) whose larger outer diameter matches the inner diameter of the main fluid channel (5) of the spirometer (1) and whose smaller inner diameter defines a central opening (here depicted as a circle); and a plurality of ribs (8.3) extending from said outer ring (8.4) towards the center of this central opening, and overlapping there in such a way that the circle is dissected across its complete diameter by the ribs (8.3). In other words, the ribs (8.3) contact the outer ring (8.4) of the perforated disk (8.1) at two points, thereby forming perforations shaped as sectors of a circle.

Figure 3D:
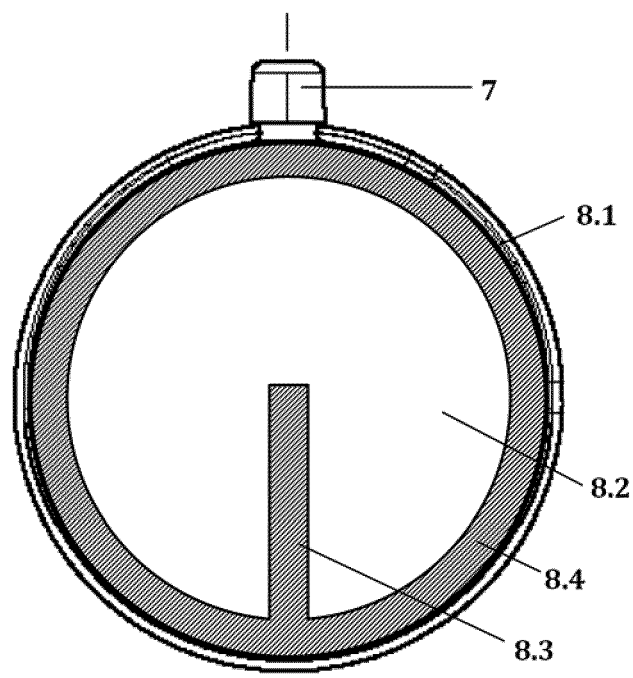

FIG. 3D shows an alternative perforated disk (8.1) with a single, irregularly shaped perforation (8.2) formed by an outer ring (8.4) and a single rib (8.3) which dissects the central opening formed in/by the outer ring (8.4) only partially; i.e. the rib (8.3) contacts the outer ring (8.4) only at one point, while the opposite end is free.

Figure 4:
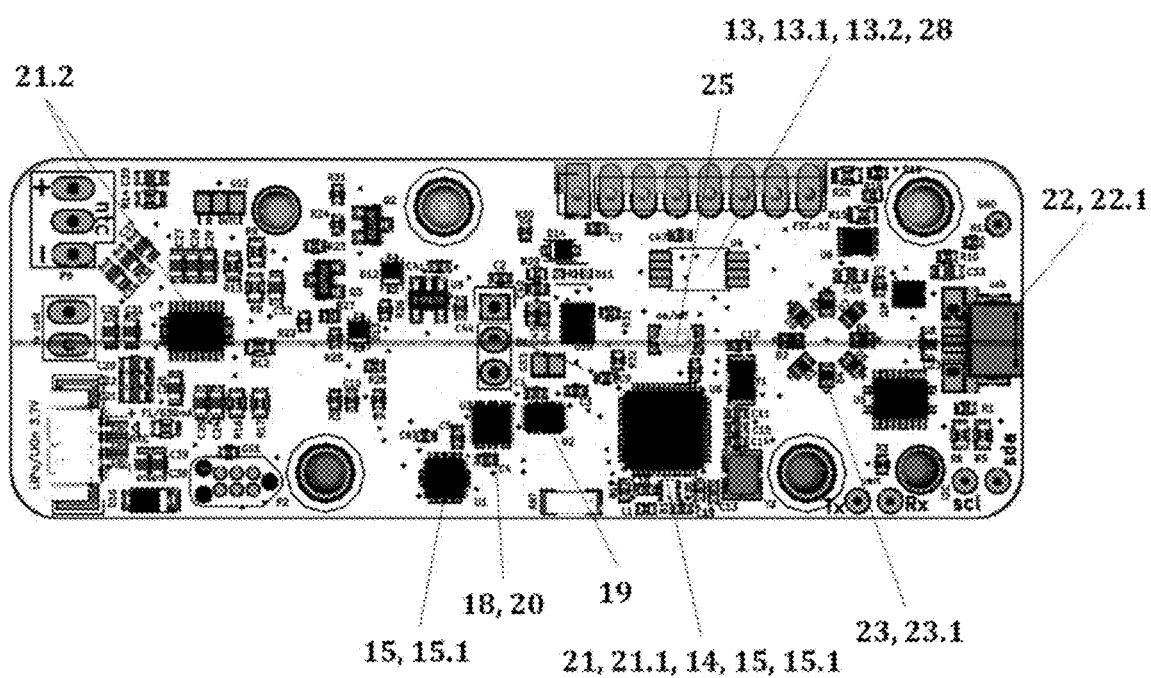

FIG. 4 shows the main board (27) of one embodiment of the spirometer (1) in top view as well as the positions of the sensors (13, 13.1, 13.2, 15, 15.1, 18, 19, 20, 28), the micro-controller (14), the radio communication means (21, 21.1), the NFC means (21.2), the cable communication means (22, 22.1), and the optical signalling means (23, 23.1).

Figure 5:
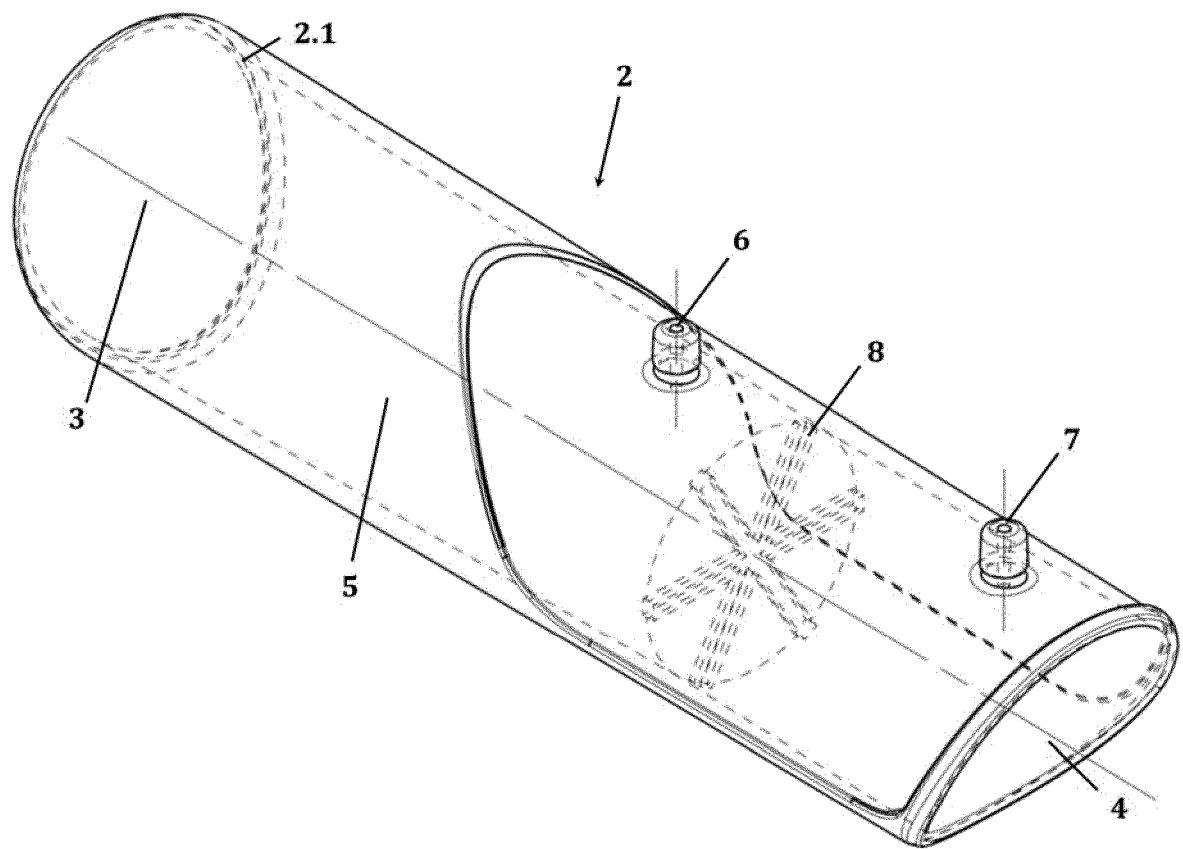

FIG. 5 shows a further embodiment of the tubular mouthpiece (2) of the spirometer (1) in perspective view. The mouthpiece (2) comprises a proximal (3) and a distal opening (4) with a main fluid channel (5) extending therebetween, a first and a second lateral opening (6 and 7) as well as a flow restrictor (8) positioned in the main fluid channel (5) perpendicular to the channel's longitudinal axis the and between the two lateral openings (6 and 7). In the depicted embodiment, the flow restrictor (8) is a perforated disk (8.2) with 6 perforations (8.2) which are shaped as sectors of a circle, with said circle being dissected across its complete diameter by straight ribs (8.3), as can be seen in more detail in FIG. 3C.

DEFINITIONS

The following terms or expressions as used herein should normally be interpreted as outlined in this section, unless defined otherwise by the description or unless the specific context indicates or requires otherwise:

All technical terms as used herein shall be understood to have the same meaning as is commonly understood by a person skilled in the relevant technical field.

The words 'comprise', 'comprises' and 'comprising' and similar expressions are to be construed in an open and inclusive sense, as 'including, but not limited to' in this description and in the claims.

The singular forms 'a', 'an' and 'the' should be understood as to include plural referents. In other words, all references to singular characteristics or limitations of the present disclosure shall include the corresponding plural characteristic or limitation, and vice versa. The terms 'a', 'an' and 'the' hence have the same meaning as 'at least one' or as 'one or more'. For example, reference to 'an ingredient' includes mixtures of ingredients, and the like.

The expressions, 'one embodiment', 'an embodiment', 'a specific embodiment' and the like mean that a particular feature, property or characteristic, or a particular group or combination of features, properties or characteristics, as referred to in combination with the respective expression, is present in at least one of the embodiments of the invention. These expressions, occurring in various places throughout this description, do not necessarily refer to the same embodiment. Moreover, the particular features, properties or characteristics may be combined in any suitable manner in one or more embodiments.

All percentages, parts and/or ratios in the context of numbers should be understood as relative to the total number of the respective items, unless otherwise specified, or indicated or required by the context. Furthermore, all percentages parts and/or ratios are intended to be by weight of the total weight; e.g. '%' should be read as 'wt.-%', unless otherwise specified, or indicated or required by the context.

'Essentially', 'about', 'approximately' (approx.), 'circa' (ca.) and the like in connection with an attribute or value include the exact attribute or the precise value, as well as any attribute or value typically considered to fall within a nonnal range or variability accepted in the technical field concerned.

'Front' as well as all similar terms designating a position, orientation or direction, such as 'left', 'right', 'rear' 'back', 'top', 'bottom', 'up', 'down' and the like, should be understood with reference to the orientation of the spirometer or its components under normal operational conditions. 'Lateral', or 'laterally', means away front the middle, centre, or centre axis of a device or device component.

The terms 'sensor' and 'transducer' are used synonymously herein, unless where specified otherwise, and refer to means which are capable of measuring a parameter (for instance, a force, a temperature or a sound) and transmitting a related signal to a data analysis unit, e.g. an electric signal which can be received, read, stored and analysed by a computer or a similar data analysis unit. In that regard, it should be understood that wordings such as 'a signal obtained from a sensor . . . ' strictly speaking refers to the signal as transmitted to the computer, and thus not necessarily to the actual measured parameter, or measurand, such as a force which triggered the respective signal.

The term 'spirometry' or 'full spirometry' refers to the entirety of measurements related to the breathing capacities, or pulmonary function, of the lungs of a breathing subject, both during inhalation or exhalation, as well as during forced or quiet breathing manoeuvres. These measurements are done both qualitatively as well as quantitatively. The term 'spirometer' as used herein thus refers to devices which are capable to perform these measurements. Examples of the most common parameters measured in (full) spirometry are vital capacity (VC), forced vital capacity (FVC), forced inspiratory vital capacity (FIVC), forced expiratory volume (FEV) at timed intervals in seconds (e.g. $FEV_1$=FEV in 1 second), forced expiratory flow (FEF), peak expiratory flow (PEF; also called peak flow), forced expiratory time (FET) and maximal voluntary ventilation (MVV; also called maximum breathing capacity). In other words, spirometry includes, or encompasses, peak flow measurements; therefore, it is understood that the spirometer according to the present invention may also be employed as a peak flow meter, while not being limited to this functionality alone. The vice-versa case is not necessarily valid; i.e. a peak flow meter is not a spirometer if limited to the functionality of measuring peak flows. Likewise, while the 'spirometers' in the sense of the present invention could in theory be employed for so-called incentive spirometry (a technique in which a subject is instructed to repeatedly inhale slowly and optionally hold its breath in order to inflate the lungs and keep the small airways open, e.g. after lung surgery or in bed-ridden patients), not every incentive spirometer can necessarily perform the above described qualitative and quantitative measurements of lung function parameters, and hence does not necessarily qualify as a 'spirometer' in the sense of the present invention, despite the similarity in names.

The term 'portable' as used herein refers to products, in particular spirometers, whose size and weight renders them suitable to be carried comfortably and for extended periods of time (such as the whole day and/or on a daily basis) by human users of said product without additional help; for instance, by simply holding it in one hand or by placing it in the pockets of trousers or coats or in a handbag. Hence, terms such as pocket-sized and/or handheld are understood to be synonymous. Typically, products with a size of about 200×60×50 mm or smaller and an overall weight of about 250 g or lighter, preferably about 150 g or even about 100 g or lighter, are considered portable. The term 'portable' further means that, during use and/or "on the go", the device is fully operable without an attached cable power source and/or without the need to be connected to a stationary workstation (such as a dedicated docking station, personal computer, or the like); for instance, the portable spirometer of the invention does not need to be plugged into a power socket for the user to be able to perform full spirometry measurements. So-called table-top devices, in particular table-top spirometers, as commonly employed in clinical settings, are not considered 'portable' in the sense of the present invention. While theoretically some of these table-top devices could still be lifted and carried around by a human user without additional help, too, it would typically not be considered comfortable for longer times (e.g. a whole day), and/or would require the use of a dedicated casing (e.g. a suitcase) and/or the use of both hands.

Any reference signs in the claims should not be construed as a limitation to the embodiments represented in any of the drawings.

DETAILED DESCRIPTION OF THE INVENTION

Figure 2:
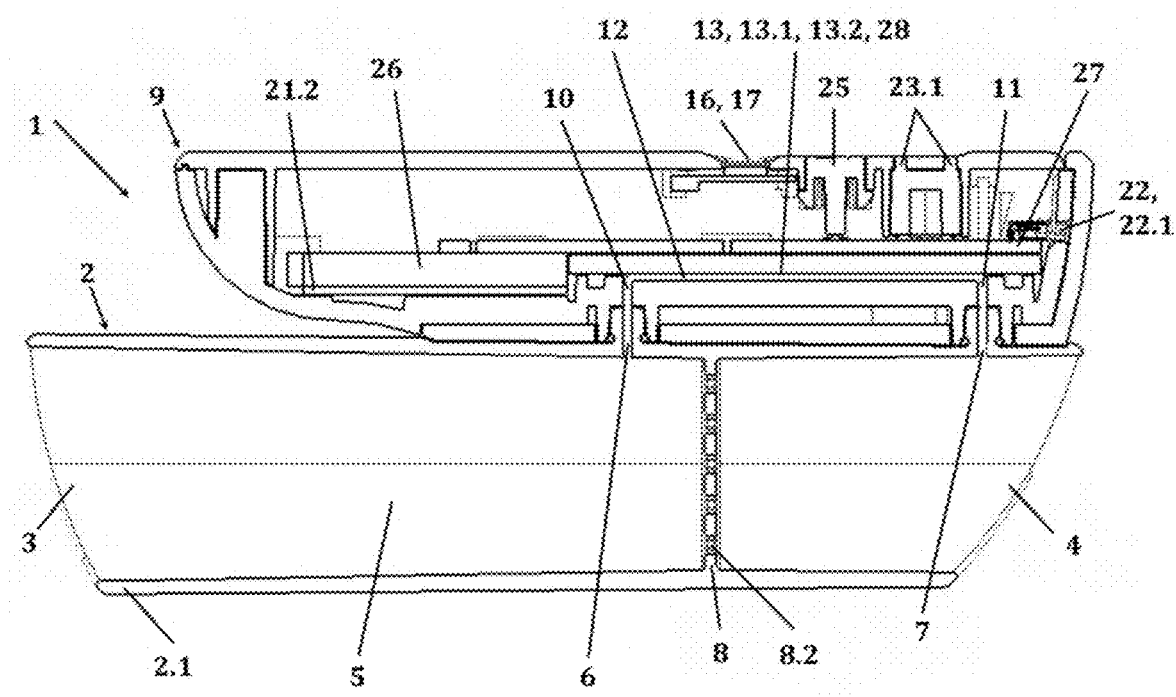
FIG. 2 shows a perspective crosssection of one embodiment of the spirometer (1). On top of the tubular mouthpiece (2) with the main fluid channel (5), the flow restrictor (8), and the first and second lateral opening (6 and 7) sits a detachable main body (9) with a first and a second fluid opening (10 and 11) and a bypass fluid channel (12) extending therebetween. A MEMS-based thermal fluid flow sensor (13, 13.1, 13.2), which also acts as a breath temperature sensor (28), is positioned at the top side, or upper side, of the bypass fluid channel (12). In the depicted version, the first and the second fluid opening (10 and 11) are connected to the first and second lateral opening (6 and 7) of the tubular mouthpiece (2).

In a first aspect, the invention provides a portable electronic spirometer (1) comprising (a) a tubular mouthpiece (2) with a proximal opening (3) for insertion into the mouth of a user, a distal opening (4), a main fluid channel (5) extending between the proximal opening (3) and the distal opening (4), a first lateral opening (6), a second lateral opening (7) positioned at a longitudinal distance to the first, and a flow restrictor (8) positioned in the main fluid channel (5) between the first and the second lateral opening (6 and 7); and (b) a main body (9) with a first fluid opening (10) connectible with the first lateral opening (6) of the mouthpiece (2), a second fluid opening (11) connectible with the second lateral opening (7) of the mouthpiece (2), a bypass fluid channel (12) extending between the first and the second fluid opening (10 and 11), a MEMS-based thermal fluid flow sensor (13) which is positioned at the bypass fluid channel (12) for generating a signal in response to the fluid flow in the bypass fluid channel (12), and a microcontroller (14) connected with the fluid flow sensor (13) for calculating the fluid flow from the signal generated by the flow sensor (13). One embodiment of this spirometer (1) is depicted in FIG. 2 for instance.

Optionally, the tubular mouthpiece (2) and the main body (9) may be detachable from one another. Further optionally, the connection between the first fluid opening (10) of the main body (9) with the first lateral opening (6) of the mouthpiece (2) and/or between the second fluid opening (11) of the main body (9) with the second lateral opening (7) of the mouthpiece (2) may be achieved by a snap-fit mechanism. Preferably, the mouthpiece (2) is designed to fit the main body (9) in only one way, or direction; preventing misplacement and/or incorrect assembly of the two parts.

One advantage of the spirometer (1) is that at a size of about 115×55×45 mm and a weight below 100 g, the device is both light weight and small, pocket-sized, handheld and thus easily portable by a user (e.g. in a coat pocket, trousers pocket or a handbag), while at the same time allowing for full spirometry as defined by the spirometry standards of the American Thoracic Society (ATS), the European Respiratory Society (see e.g. Eur Respir J 1997; 10: Suppl. 24, 2s-8s; or "Standardisation of spirometry"; Eur Respir J 2005; 26: 319-338) or ISO 26782:2009 (specifying the requirements for spirometers intended for the assessment of pulmonary function in humans weighing more than 10 kg) at very high precision; including measurements during both inhalation and exhalation and providing all functions of spirometers as used in hospital settings. The device is further capable to fulfil the peak expiratory flow statement by the ERS (see e.g. "Peak expiratory flow: conclusions and recommendations of a Working Party of the European Respiratory Society").

The basic functionality of the spirometer (1) includes the measurement of exhalatory and inspiratory fluid flow rates, time and volume of exhalation and inspiration, as well as calculation of all spirometric parameters of interest, including the most common: FVC, $FEV_1$, PEF and $FEV_1\%$ but also parameters such as $FEV_6$, FRC, SVC, MW or ERV, in order to assess the respiratory function of a user (e.g. a patient suffering from a respiratory disease, or an athlete).

Additionally, the spirometer (1) will continuously monitor the local environmental parameters, such as temperature, pressure and ambient air humidity, as will be detailed further below. This may, for instance, be achieved by monitor the local environmental parameters at a predefined monitoring frequency, or monitoring interval (e.g. 10 seconds for every one hour, every half hour or every quarter hour, or the like). Like this, the user of the spirometer (1) not only measures and receives the spirometric data with regards to his/her lung function, but can also match specific data points to e.g. the environmental parameters at, or around, the spirometric measurement time point.

A further advantage is that the spirometer (1) may be used by lay people, i.e. without medical or similarly trained staff as currently required for most spirometry tests in doctor's offices and/or hospital settings; thus providing users with an 'in-home' spirometer which they can use by themselves. In that regard, it should be understood that in the context of this invention, users are not necessarily patients afflicted with respiratory diseases. The parameters used to examine the respiratory tract are also helpful e.g. for athletes training regularly, enabling them to monitor their training progress and track their performance; or for smokers wanting to evaluate the benefits of their smoking cessation.

Advantageously, the spirometer (1) may be connected to a user's personal computer and/or smartphone, preferably via a dedicated proprietary spirometer application ('app') with proprietary and predictive algorithms; or as an 'add-on' integrated in existing healthcare apps available for iOS or Android smartphones.

Furthermore, the spirometer (1) of the invention is fully electronic and does not comprise any moving parts, such as rotating turbines or oscillating cantilevers as they are common for measuring the fluid flow in prior art spirometers, thus obviating the need for regular, frequent external calibrations. Further, it turns on quickly with less than 7 seconds between switching the spirometer (1) on and the device being ready for use. This is not only energy-efficient and thus saving battery life, but also renders the device suited to be used "on the go" by medical staff such as doctors; for instance, during ward rounds, home visits, etc.

MEMS-based thermal fluid flow sensors (13) provide a high sensitivity for fluid flow measurements, yet at the same time suffer from an inherent detrimental susceptibility to vibration; i.e. any flow measurement attempts are per se affected by non-flow-related vibrations as they occur e.g. when the user moves the spirometer during use. This may be one of the reasons, why—according to the current knowledge of the inventors—no operable, fully functional spirometer comprising a MEMS-based thermal fluid flow sensor has actually been developed before. The invention is based on the unexpected discovery that a MEMS-based thermal fluid flow sensor (13) can be incorporated in a portable electronic spirometer in such a way that accurate and reproducible, or precise, (full) spirometric flow measurements are enabled, and unlike many other devices further allows both inspiratory and expiratory lung function assessments. This is achieved by positioning the MEMS-based thermal fluid flow sensor (13) at a bypass fluid channel (12) and providing a flow restrictor (8) in order to redirect specific fractions of the air flow in the main fluid channel (5) to the bypass fluid channel (12). When incorporated in the spirometer (1) in this way, the MEMS-based thermal fluid flow sensor (13) provides a higher precision, reproducibility and sensitivity than the different flow sensors typically used in prior art portable spirometers, such as fan-based transducers (turbines). Additionally, by placing the MEMS-based thermal fluid flow sensor (13) in the bypass fluid channel (12) comprised in the main body (9) of the spirometer (1), it is protected from direct exposure to saliva and/or bioparticles that could damage it, or affect the accuracy and/or precision of measurements.

The precision, reproducibility and sensitivity may be increased further by using an acceleration sensor (15) which is not connected to the main fluid channel (5) or the bypass fluid channel (12) in addition to the MEMS-based thermal fluid flow sensor (13). This acceleration sensor (15), preferably an acceleration sensor (15) which is incorporated within the portable electronic spirometer (1), in particular within the main body (9) the portable electronic spirometer (1), allows for the correction of the calculated fluid flow as will be detailed further below. The acceleration sensor (15) further allows for alerting the user if movement is detected during measurements and, if needed, to instruct the user to correct his/her position, and/or to disregard incorrectly performed manoeuvres in longterm analysis (e.g. manoeuvres with substantial head movement); thereby improving the quality of the single manoeuvre as well as the longterm analysis of lung function parameters. In final consequence, the acceleration sensor (15) also allows for a clinically relevant improvement of the sensitivity, accuracy, and reproducibility, or precision, of the spirometric flow measurements of the spirometer (1).

In one embodiment, the mean accuracy of the spirometer (1) fulfills ATS/ERS criteria; i.e. the parameters determined with the spirometer (1) of the invention differ not more than the allowed values from the reference flow curves (see accuracy tests for spirometers in "Standardisation of spirometry"; Eur Respir J 2005; 26: 319-338, on page 333; or ISO 26782:2009 which specifies requirements for spirometers intended for the assessment of pulmonary function in humans weighing >10 kg). Even at low flow rates below 0.3 L/sec, the accuracy is maximally ±3%. The repeatability, or in other words the reproducibility or precision, is ±0.5%.

In fact, the use of a MEMS-based thermal fluid flow sensor (13) in the spirometer (1) of the invention as claimed, and preferably a spirometer (1) with an incorporated acceleration sensor (15) which is not connected to the main fluid channel (5) or the bypass fluid channel (12) in addition to said MEMS-based thermal fluid flow sensor (13), renders the device sensitive enough to even measure the minute movements of air moved in or out of the trachea by the heart beat, enabling new medical uses which were not available before with prior art spirometers.

A yet further advantage of the inventive spirometer (1), in particular, for embodiments where the mouthpiece (2) and the main body (9) are detachable from one another, is that because the MEMS-based thermal fluid flow sensor (13) is positioned at the bypass fluid channel (12) comprised in the main body (9), the mouthpiece (2) may be detached easily and safely from the main body (9) without the risk of potentially damaging said flow sensor (13), or otherwise affecting the accuracy and/or precision of its measurements. This overcomes the limitations of prior art devices in which only the accurate (re)placement of a detachable mouthpiece into a main body ensured proper functioning as well as accuracy and precision of the flow sensor, e.g. a pressure sensor. The spirometer (1) of the invention comprises a mouthpiece (2) designed to fit the main body (9) in only one way, or direction; preventing misplacement and/or incorrect assembly of the two parts, as described above.

The main fluid channel (5) of the tubular mouthpiece (2) is typically shaped as a hollow circular cylinder or as an elliptical cylinder, partially in order to resemble the shape of the opened mouth of a user upon inhaling or exhaling through the main fluid channel. Optionally, the cylinder may be slightly tapered towards the distal opening (4); for instance, gradually narrowing from an outer diameter of about 31 mm at the proximal opening (3) to an outer diameter of about 29 mm at the distal opening (4) over a length of about 110 to 120 mm.

In general, the diameter of the main fluid channel (5) at the proximal opening (3) should be chosen such as to comfortably fit the mouth of the intended user and allow him/her to effectively seal the mouthpiece (2) with the lips. For instance, a diameter at the proximal opening (3) of about 30 mm for adult users would be suitable and smaller diameters for infants or kids. Optionally, a small groove, or ridge, may be provided for the user's teeth in order to improve the seal between lips and mouthpiece (2).

Figure 1A:
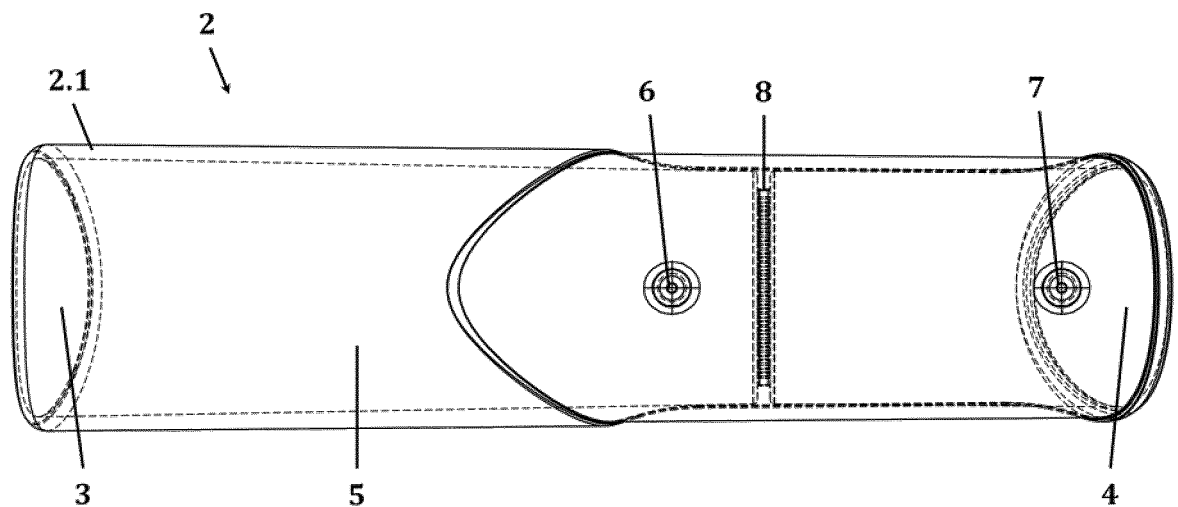
FIGS. 1A-C show one embodiment of the tubular mouthpiece (2) of the spirometer (1) in top view (A), side view (B) and in perspective view (C). The mouthpiece (2) comprises a proximal (3) and a distal opening (4) with a main fluid channel (5) extending therebetween, a first and a second lateral opening (6 and 7) as well as a flow restrictor (8) positioned in the main fluid channel (5) perpendicular to the channel's longitudinal axis the and between the two lateral openings (6 and 7). In the depicted embodiment, the flow restrictor (8) is a perforated disk (8.1) with 55 hexagonal perforations, as can be seen in more detail in FIG. 3A.
Figure 1B:
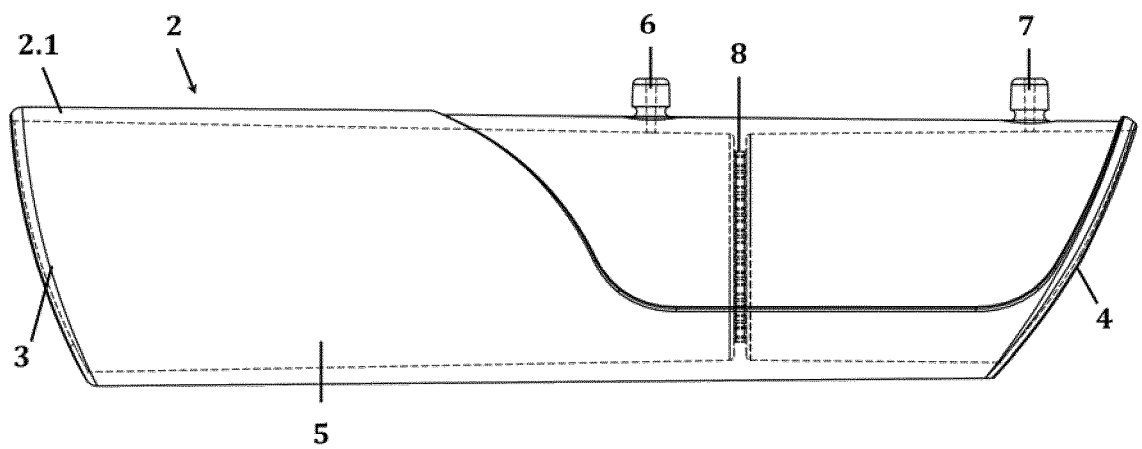
Figure 1C:
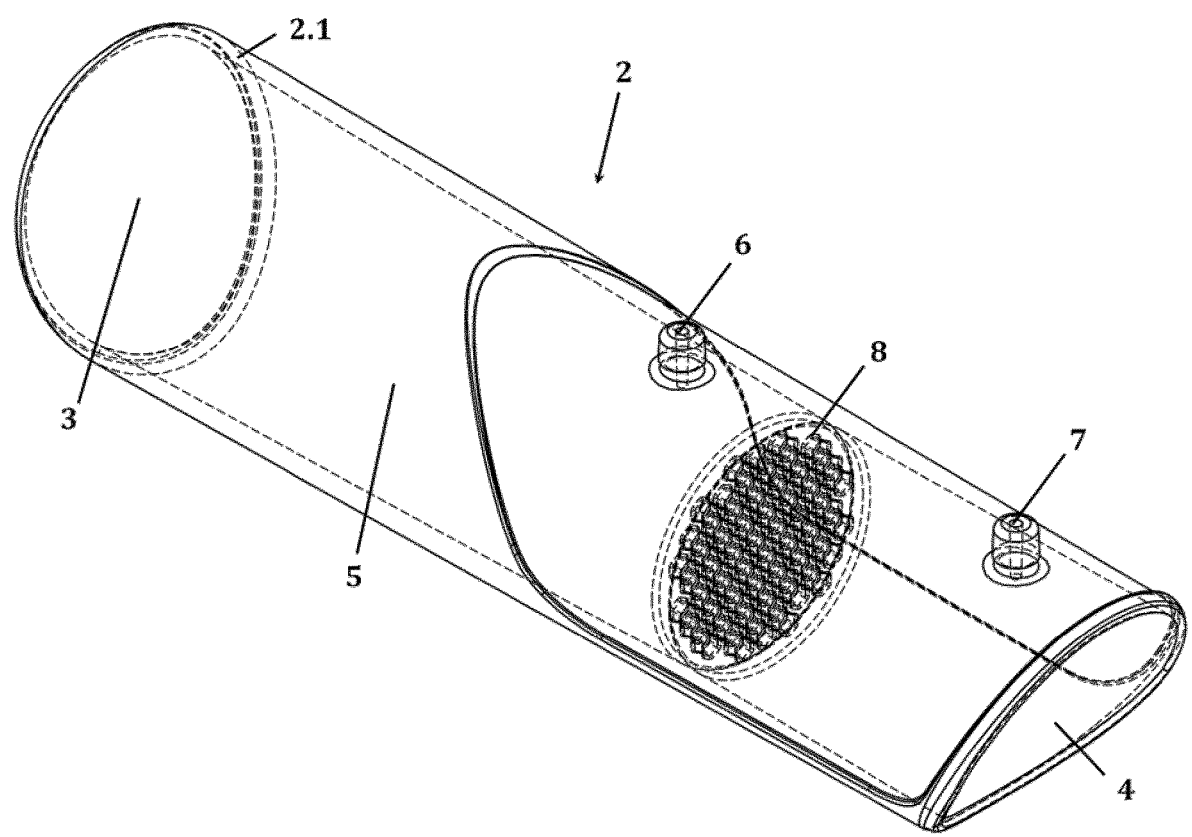

In the embodiment as depicted in FIG. 1A-C, the front end (2.1) of the tubular mouthpiece (2), i.e. the end comprising the proximal opening (3) is configured as an integral part of the tubular mouthpiece (2). Alternatively, this front end (2.1) may be configured as a detachable part of the tubular mouthpiece (2), allowing to remove this front end (2.1) portion of the mouthpiece (2) in order to either clean it, or discard and replace it, after contact with a user's lips and/or tongue. A detachable front end (2.1) facilitates cleaning and enables the use of disposable parts in multi-patient settings (where applicable).

As mentioned, the flow restrictor (8) is an integral part of the spirometer (1) which—in combination with the bypass fluid channel (12)—enables accurate and reproducible, or precise, measurements of the air flow in the main fluid channel (5) by the MEMS-based thermal fluid flow sensor (13; or hereafter also shortly referred to as the flow sensor (13)).

The flow restrictor (8) is employed in order to direct some of the fluid flow, namely the inhaled or exhaled air stream, which passes through the main fluid channel (5) into the bypass fluid channel (12) and past the flow sensor (13). This is important because the flow sensor (13) is highly sensitive; i.e. by redirecting only a fraction of the fluid flow in the main fluid channel (5) through the bypass fluid channel (12), the flow sensor (13) is enabled to generate signals which have a high correlation with the fluid flow in the main fluid channel (5). Furthermore, the flow sensor (13) is sensitive to vibrations, or noises, which may result from a movement or acceleration of the device; therefore, shielding it from the main fluid channel (5) further helps to ensure precise and accurate fluid flow measurements.

In one embodiment, the flow restrictor (8) in the spirometer (1) exhibits a flow resistance, or impedance, in the range from about 0.01 to about 0.2 kPa/(L/s), preferably from about 0.01 to about 0.15 kPa/(L/s), and more preferably from about 0.01 to about 0.1 kPa/(L/s) at a fluid flow of 60 SLM to 900 SLM (or SLPM; standard liter per minute); and/or the flow restrictor (8) is adapted or configured such as to cause a fluid flow in the bypass fluid channel (12) which is from about 1:10 to about 1:200 of the fluid flow in the main fluid channel (5). In other word, the fluid flow in the bypass channel (12) may range from about 0.3 SLM to about 90 SLM. The flow resistance thus falls below the maximum value of 0.15 kPa/(L/s) at a fluid flow of 840 SLM as required by the "Standardisation of spirometry" (as published e.g. by the American Thoracic Society (ATS) or the European Respiratory Society (ERS) in Eur Respir J 2005; 26: 319-338).

In one embodiment, the flow restrictor (8) is a perforated disk (8.1) having a cross-sectional orientation with respect to the main fluid channel (5), i.e. a fixed, or immobile or immovable, mechanical flow restrictor (8) which is being arranged perpendicular to the main fluid channel's (5) longitudinal axis and having a diameter matching the inner diameter of the channel (5), such as to allow fluid flow only through the perforations (8.2) of the disk (8.1). In other words, the portable electronic spirometer (1) of this embodiment comprises:

(a) a tubular mouthpiece (2) with a proximal opening (3) for insertion into the mouth of a user, a distal opening (4), a main fluid channel (5) extending between the proximal opening (3) and the distal opening (4), a first lateral opening (6), a second lateral opening (7) positioned at a longitudinal distance to the first lateral opening (6), and a flow restrictor (8) positioned in the main fluid channel (5) between the first and the second lateral opening (6 and 7), wherein said flow restrictor (8) is a perforated disk (8.1) having a cross-sectional orientation with respect to the main fluid channel (5); and (b) a main body (9) with a first fluid opening (10) connectible with the first lateral opening (6) of the mouthpiece (2), a second fluid opening (11) connectible with the second lateral opening (7) of the mouthpiece (2), a bypass fluid channel (12) extending between the first and the second fluid opening (10 and 11), a MEMS-based thermal fluid flow sensor (13, 13.1, 13.2) positioned at the bypass fluid channel (12) for generating a signal in response to the fluid flow in the bypass fluid channel (12), and a microcontroller (14) connected with the fluid flow sensor (13, 13.1, 13.2) for calculating the fluid flow from the signal generated by the flow sensor (13, 13.1, 13.2). A perforated disk (8) is advantageous, for instance, in comparison to a venturi section in the flow channel, in that it can be exchanged more easily to e.g. adjust flow restriction values (such as for adults, kids, infants). Optionally, the mouthpiece (2) may comprise a dedicated groove into which the perforated disk (8) can be slid such as to be fixed, or immobilized, within the mouthpiece (2) during transport and/or use of the spirometer (1). The perforated disk (8) further allows to sustain a laminar air flow which is vital to avoid unpredicted turbulences in the main fluid channel (5) and the bypass fluid channel (12).

In one embodiment, the perforated disk (8.1) exhibits from about 1 to about 100 perforations, or from about 2 to about 100 perforations, or from about 4 to about 100 perforations (8.2), or from about 15 to about 100 perforations (8.2). For instance, the perforated disk (8.1) may exhibit from about 1 to about 24 perforations, or from about 2 to about 21 perforations, or from about 4 to about 18 perforations, or from about 6 to about 12 perforations; or from about 30 to about 85 perforations, or from about 45 to about 70 perforations. These perforations (8.2) may be shaped as sectors of a circle or oval; or they may be circular, elliptic or polygonal in shape; or they may exhibit an irregular shape. Optionally, perforations of more than one shape may be combined with each other Alternatively or in addition, these perforations (8.2) may exhibit a total combined area of all perforations (8.2) ranging from about 26% to about 96%, or from about 39% to about 96%, or from about 26% to about 72%, of the cross-sectional area of the main fluid channel (5) at the position of the perforated disk (8.1). In other words from about 26% to about 96%, or from about 39% to about 96%, or from about 26% to about 72%, of the cross-sectional area of the perforated disk (8.1) is open/perforated (this area also being referred to herein as the 'perforated area'); such as from about 30% to about 96%, or from about 39% to about 96% (e.g. about 39%, or about 76%, or about 96%), or from about 30% to about 60%, or from about 30% to about 50% (e.g. about 30%), or from about 40% to about 50% (e.g. about 43% or about 45%).

The smaller 'perforated areas' values from about 30% to about 60% are more common, though not exclusively, for perforated disks (8.1) exhibiting a multitude of circular or hexagonal perforations (e.g. in the range from about 15 to about 100 perforations). The larger 'perforated areas' values from about 60% to about 96% are more common, though not exclusively, for perforated disks (8.1) exhibiting fewer but larger perforations.

For all embodiments, the 'perforated area' is controllable via the adjustment of the number of perforations and/or the adjustment of the size, or surface area, of the perforations. For the embodiments, where the perforation(s) is/are shaped by a rib (8.3), or a plurality of ribs (8.3), the 'perforated area' is controllable via the adjustment of the number of ribs and/or the adjustment of their size, or surface area, of the ribs.

In a specific embodiment, the flow restrictor (8) is a perforated disk (8.1) with about 35 to about 80, or about 45 to about 70, perforations (8.2) exhibiting a 'perforated surface area' of from about 26% to about 96% of the perforated disk's (8.1) total surface area. In a further specific embodiment, the flow restrictor (8) is a perforated disk (8.1) with a total surface area of about 587 mm$^2$ and 55 perforations (8.2) exhibiting a 'perforated surface area' of about 175 mm$^2$, or about 30% of the perforated disk's (8.1) total surface area. In a yet further specific embodiment, the perforations (8.2) are shaped as regular hexagons, as depicted exemplarily in FIG. 3A.

In another specific embodiment, the flow restrictor (8) is a perforated disk (8.1) with a total surface area of about 587 mm$^2$ and 37 perforations (8.2) exhibiting a 'perforated surface area' of about 262 mm$^2$, or about 45% of the perforated disk's (8.1) total surface area. In a more specific embodiment, the perforations (8.2) exhibit a circular shape, as depicted exemplarily in FIG. 3B.

In a further specific embodiment, the flow restrictor (8) is a perforated disk (8.1) where the perforations are shaped as sectors of a circle or oval, said sectors being formed by a rib, or ribs (8.3), which dissect(s) a circular or oval opening, across its complete diameter, forming perforations (8.2) shaped as sectors of a circle, or oval. This circular or oval opening may be formed by an internal crosssection of the main fluid channel (5). Alternatively, the perforated disk (8.1) may comprise an outer ring (8.4) whose larger outer diameter matches the inner diameter of the main fluid channel (5) of the spirometer (1) and whose smaller inner diameter defines a central opening (e.g. a circular or oval opening). In this embodiment, the rib, or ribs (8.3), may extend from the outer ring (8.4), with each rib (8.3) contacting the ring (8.4) at two points, such that the circular, or oval, central opening is dissected across its complete diameter by the ribs (8.3), and perforations (8.2) shaped as sectors of a circle, or oval, are formed (as depicted exemplarily in FIG. 3C). Further alternatively, the rib, or ribs (8.3) may extend from said outer ring (8.4) towards the center of said central opening, but with each rib (8.3) contacting the outer ring (8.4) at only one point, thereby dissecting the central opening only partially rather than completely, and forming irregularly shaped perforations (8.2), as depicted exemplarily in FIG. 3D.

Where the perforations are shaped as sectors of a circle, or oval, the ribs (8.3) dissecting said circle, or oval, across its complete diameter may have a breadth of from about 0.1 mm to about 4 mm, or from about 1 mm to about 3 mm, or from about 1.5 mm to about 2.5 mm, such as 1.9 mm, 1.95 mm or 2 mm. These ribs (8.3) may be straight as depicted e.g. in FIG. 3C.

For embodiments where the rib, or ribs (8.3), do not extend across the complete diameter (e.g. as depicted in FIG. 3D) the rib, or ribs, may be even broader; for instance, from about 0.1 mm to about 15 mm, or from about 1 mm to about 12 mm, or from about 1.5 mm to about 10 mm, or from about 1.7 mm to about 8 mm, or from about 2 mm to about 6 mm. This rib, or these ribs (8.3), may be straight as depicted in FIG. 3D. Further, this rib, or these ribs (8.3), may exhibit a rectangular shape, also as depicted in FIG. 3D.

In a specific embodiment, the flow restrictor (8) is a perforated disk (8.1) with a total surface area of about 587 mm$^2$ and 1-6 perforation(s) (8.2), dissected by ribs (8.3) and exhibiting a 'perforated surface area' of about 232-562 mm$^2$, or about 39-96% of the perforated disk's (8.1) total surface area. In a further specific embodiment, the flow restrictor (8) is a perforated disk (8.1) with a total surface area of about 587 mm$^2$ and 1-6 perforation(s) (8.2), dissected by ribs (8.3), the disk (8.1) exhibiting a 'perforated surface area' of about 447 mm$^2$, or about 76% of the perforated disk's (8.1) total surface area. In a more specific embodiment, the flow restrictor (8) is a perforated disk (8.1) with a total surface area of about 587 mm$^2$ and 2-6 perforations (8.2) which are shaped as sectors of a circle or oval; for instance, 6 perforations (8.2) dissected by 3 ribs (8.3) which extend from an outer ring (8.4) as depicted exemplarily in FIG. 3C.

The embodiments using a rib, or ribs (8.3) to define the size and shape of the perforations (8.2) may be preferred in that they allow very smooth airflow with little turbulence, and a signal with limited noise in the main fluid channel (5). In addition, they are typically easy to prepare using, for instance, molding or 3D-printing techniques.

With regard to the 'perforated area' of the perforated disk (8.1), it should be understood that this area also depends on the dimensions of the bypass fluid channel (12), or is adjusted in relation thereto. If e.g. the crosssectional area of the bypass fluid channel (12) is larger, more air may be redirected there; so, the perforated disk (8.1) should exhibit a larger 'perforated area' as well. In one embodiment, the ratio of the 'perforated area' of the perforated disk (8.1) to the crosssectional area of the bypass fluid channel (12) ranges from about 150 to about 350, such as 250. However, it should be understood, that the exact ratio of the 'perforated area' of the perforated disk (8.1) to the crossectional area of the bypass fluid channel (12) is of lower relevance as long as the flow restrictor (8) causes a fluid flow in the bypass fluid channel (12) which is from about 1:10 to about 1:200 of the fluid flow in the main fluid channel (5) and/or ranging from about 0.3 SLM to about 90 SLM.

The perforated disks (8.1) may be prepared by any technique suited to provide perforations of the desired shape and size which is needed for providing a flow resistance, or impedance, in the range from about 0.01 to about 0.2 kPa/(L/s); and/or to cause a fluid flow in the bypass fluid channel (12) which is from about 1:10 to about 1:200 of the fluid flow in the main fluid channel (5). This can be achieved for instance by cutting or die-cutting the perforations (8.2) into the disk (8.1) using e.g. a laser cutter or water jet cutter, a die cutter, a punch, or the like. Alternatively, the disk (8.1) may be molded or otherwise 'positively' formed, such as by 3D-printing techniques. In other words, the term 'perforation' is used herein synonymously to 'opening', or 'hole' or the like, and is not intended to imply a specific preparation method which necessarily involves cutting, punching or stamping or similar techniques which form the perforations by removing material from the blank disk.

In order to advantageously allow molding the perforated disk (8.1) as one single piece, it was modified in comparison to those used in e.g. industrial gas flow measurement applications. In one embodiment, the flow restrictor (8) is a perforated disk (8.1) with a width, or thickness, of about 2 to 4 mm. In a further embodiment, the perforated disk (8.1) is molded or 3D-printed and exhibits a width, or thickness, of about 1 to 4 mm. In a yet further embodiment, the perforated disk (8.1) exhibits a width, or thickness, of about 1 to 4 mm, a total surface area of about 587 mm$^2$ and 2 to 6 perforations (8.2) shaped as sectors of a circle or oval, dissected by straight ribs (8.3) with a width of about 1.5 mm to about 2.5 mm (e.g. 1.9 mm or 2 mm); and a 'perforated surface area' of about 39 to 96% (e.g. 76%) of the perforated disk's (8.1) total surface area. Perforated disks (8.1) with straight ribs dissecting a circle, or oval, into sectors (e.g. into 6 sectors) may be preferred in that they are typically easy to mold or print.

In one embodiment, the distance between the flow restrictor (8) and the first lateral opening (6) along the longitudinal axis of the main fluid channel (5) of the spirometer (1) is from about 5 mm to about 15 mm, and preferably from about 8 mm to about 12 mm, e.g. 10.0 mm; and the distance between the flow restrictor (8) and the second lateral opening (7) from about 25 mm to about 45 mm, and preferably from about 30 mm to about 40 mm, e.g. 34.2 mm. However, it should be understood, that the exact spacing of the flow restrictor (8) between the first and second lateral opening (6 and 7) is of lower relevance as long as the flow restrictor (8) causes a fluid flow in the bypass fluid channel (12) which is from about 1:10 to about 1:200 of the fluid flow in the main fluid channel (5) and/or ranging from about 0.3 SLM to about 90 SLM.

In one embodiment, the MEMS-based thermal fluid flow sensor (13) of the spirometer (1) is a bidirectional flow sensor (13.1), such as to allow e.g. for measurements during both inhalation and exhalation. In this configuration, the MEMS-based thermal fluid flow sensor (13, 13.1) enables the determination of all relevant spirometry parameters: FVC, FEV1, FEV$_{1\%}$, PEF, FEF$_{25-75\%}$, FET, EVOL, ELA, VC, IVC, IC, ERV, FEV$_1$/FVC$_\%$, FEV$_{0.5}$, FEV$_{0.5}$/FVC$_\%$, FEV$_{0.75}$, FEV$_{0.75}$/FVC$_\%$, FEV$_2$, FEV$_2$/FVC %, FEV$_3$, FEV$_3$/FVC$_\%$, FEV$_6$, FEV$_1$/FEV$_{6\%}$, FEF$_{25\%}$, FEF$_{0.50\%}$, FEF$_{0.75\%}$, FEF$_{75-85}$, FIVC, FIV$_1$, FIV$_1$/FIVC$_\%$, FIF$_{0.25\%}$, FIF$_{50\%}$. The most commonly evaluated parameters are FVC, FEV, FEV$_1$, PEF.

In a more specific embodiment, the MEMS-based thermal fluid flow sensor (13) is a monolithic CMOS flow sensor (13.2; complementary metal-oxide-semiconductor) comprising a sensor chip, the chip comprising an encapsulated gas bubble, a microheater for heating the gas bubble, a first plurality of thermopiles located on a first side of the gas bubble, and a second plurality of thermopiles located on a second side of the gas bubble which is opposite to the first side. In a preferred embodiment, the thermopiles are symmetrically positioned upstream and downstream of the micro-heater, such that in the presence of fluid flow, or gas flow, the thermopiles will show temperature differences from which a) the fluid flow may be calculated, and b) the exhale temperature can be determined; i.e. such a monolithic CMOS flow sensor (13.2) also acts as a breath temperature sensor (26). The sensor chip can be mounted on a printed circuit board along with e.g. the microcontroller (14) as depicted in FIG. 4.

In a specific embodiment, the communication of the MEMS-based thermal fluid flow sensor (13, 13.1, 13.2) with the microcontroller (14) is achieved via a so-called SPI bus (serial peripheral interface).

The MEMS-based thermal fluid flow sensor (13, 13.1, 13.2)—or hereafter shortly referred to as the flow sensor (13, 13.1, 13.2)—is positioned at the bypass fluid channel (12) for generating a signal in response to the fluid flow in the bypass fluid channel (12). As mentioned, the bypass fluid channel (12) extends from the first to the second fluid opening (10 and 11), and therefore—as long as the tubular mouthpiece (2) and the main body (9) of the spirometer (1) are attached to each other—also from the first to the second lateral opening (6 and 7) of the tubular mouthpiece (2), such that a fluid communication between the main fluid channel (5) and the bypass fluid channel (12) is provided. In one embodiment, the bypass fluid channel (12) has a parallel orientation to and extends over a longitudinal portion of the main fluid channel (5). This may be seen e.g. in FIG. 2.

In one embodiment, the spirometer (1) further comprises an acceleration sensor (15) which is different from the flow sensor (13, 13.1, 13.2), as shown for instance in FIG. 4. In other words, the portable electronic spirometer (1) of this embodiment comprises:

(a) a tubular mouthpiece (2) with a proximal opening (3) for insertion into the mouth of a user, a distal opening (4), a main fluid channel (5) extending between the proximal opening (3) and the distal opening (4), a first lateral opening (6), a second lateral opening (7) positioned at a longitudinal distance to the first lateral opening (6), and a flow restrictor (8) positioned in the main fluid channel (5) between the first and the second lateral opening (6 and 7); and (b) a main body (9) with a first fluid opening (10) connectible with the first lateral opening (6) of the mouthpiece (2), a second fluid opening (11) connectible with the second lateral opening (7) of the mouthpiece (2), a bypass fluid channel (12) extending between the first and the second fluid opening (10 and 11), a MEMS-based thermal fluid flow sensor (13, 13.1, 13.2) positioned at the bypass fluid channel (12) for generating a signal in response to the fluid flow in the bypass fluid channel (12), an acceleration sensor (15, 15.1) which is different from the MEMS-based thermal fluid flow sensor (13, 13.1, 13.2), and a microcontroller (14) connected with the fluid flow sensor (13, 13.1, 13.2) for calculating the fluid flow from the signal generated by the flow sensor (13, 13.1, 13.2).

It should be understood, that this acceleration sensor (15) is preferably incorporated within and/or an integral part of the spirometer (1), usually as part of the spirometer's main body (9), e.g. on the printed circuit board; in other words, the acceleration sensor (15) is not provided separate or external from the spirometer (1). This set-up is selected to ensure that, while being different from the flow sensor (13, 13.1, 13.2), the acceleration sensor (15) is still exposed to the same or very similar external influences (such as temperature, movement, vibration, etc.) as the flow sensor (13, 13.1, 13.2); and/or, to ensure that the sensitivity achieved is matching the sensitivity needed for high precision spirometry. Same as the flow sensor (13, 13.1, 13.2), this acceleration sensor (15) is directly or indirectly connected with the microcontroller (14) such that the microcontroller (14) is capable of receiving a signal from the acceleration sensor (15). The acceleration sensor (15) can, for instance, be mounted on a printed circuit board along with e.g. the flow sensor (13, 13.1, 13.2) and the microcontroller (14) as depicted in FIG. 4. However, unlike the flow sensor (13,

13.1, 13.2), this acceleration sensor (15) is not connected to the main fluid channel (5) or the bypass fluid channel (12), such as to generate signals which are predominantly related to vibrations, or noises, caused by movements, or accelerations, of the spirometer (1).

In one of the preferred embodiments, the portable electronic spirometer (1) comprises:

(a) a tubular mouthpiece (2) with a proximal opening (3) for insertion into the mouth of a user, a distal opening (4), a main fluid channel (5) extending between the proximal opening (3) and the distal opening (4), a first lateral opening (6), a second lateral opening (7) positioned at a longitudinal distance to the first lateral opening (6), and a flow restrictor (8) positioned in the main fluid channel (5) between the first and the second lateral opening (6 and 7), wherein said flow restrictor (8) is a perforated disk (8.1) having a cross-sectional orientation with respect to the main fluid channel (5); and (b) a main body (9) with a first fluid opening (10) connectible with the first lateral opening (6) of the mouthpiece (2), a second fluid opening (11) connectible with the second lateral opening (7) of the mouthpiece (2), a bypass fluid channel (12) extending between the first and the second fluid opening (10 and 11), a MEMS-based thermal fluid flow sensor (13, 13.1, 13.2) positioned at the bypass fluid channel (12) for generating a signal in response to the fluid flow in the bypass fluid channel (12), an acceleration sensor (15, 15.1) which is different from the MEMS-based thermal fluid flow sensor (13, 13.1, 13.2); and a microcontroller (14) connected with the fluid flow sensor (13, 13.1, 13.2) for calculating the fluid flow from the signal generated by the flow sensor (13, 13.1, 13.2).

The flow restricting perforated disk (8.1) in the above described preferred embodiment may be any one of the perforated disks (8.1) described earlier, preferably a perforated disk (8.1) comprising from about 2 to about 100 perforations, or from about 4 to about 100 perforations (8.2), or from about 15 to about 100 perforations (8.2); for instance, a perforated disk (8.1) with a total surface area of about 587 mm$^2$ and 55 hexagonal perforations (8.2) with a 'perforated surface area' of about 175 mm$^2$, or 37 circular perforations (8.2) with a 'perforated surface area' of about 262 mm$^2$, or 6 perforations (8.2) shaped as sectors of a circle, or oval with a 'perforated surface area' of about 447 mm$^2$.

As mentioned, the flow sensor (13, 13.1, 13.2) is rather sensitive to vibrations, or noises, resulting e.g. from a movement or acceleration of the spirometer (1). Therefore, an additional acceleration sensor (15) which is not connected to the main fluid channel (5) or the bypass fluid channel (12), but incorporated within the spirometer (1), in particular within the main body (9) of the spirometer (1), allows for the correction of the calculated fluid flow in that they detect such non-flow-related vibrations, or noises, and enable the subtraction of it from the fluid flow signal generated by the flow sensor (13, 13.1, 13.2), and/or allow for the verification that a measurement of the flow sensor (13, 13.1, 13.2) was performed under suitable conditions (such as without significant noise).

In one embodiment, the microcontroller (14) of the spirometer (1) is programmed to calculate a corrected fluid flow from the signal generated by the flow sensor (13, 13.1, 13.2) and from a signal generated by the acceleration sensor (15). In a specific embodiment, the microcontroller (14) is connected both with the fluid flow sensor (13, 13.1, 13.2) and the acceleration sensor (15, 15.1) and is programmed to calculate a corrected fluid flow from the signal generated by the flow sensor (13, 13.1, 13.2) and from a signal generated by the acceleration sensor (15, 15.1).

In a more specific embodiment, the acceleration sensor (15) is a 3-axis sensor (15.1) with a sensitivity (So) of at least 973 counts/g±5% for each of the three axes; typically, the sensitivity ranges between 973 and 1075 counts/g; e.g. 1024 counts/g; for instance, a MMA8491QR1 unit as supplied by Freescale Semidconductors. This MMA8491QR1 unit is a low voltage, multifunctional digital 3-axis, 14-bit±8 g accelerometer housed in a 3×3 mm casing and may communicate with the microcontroller (14) via a common inter-integrated circuit bus (I$^2$C bus), or I$^2$C interface. It covers an acceleration range of ±8 per axis and data may be read from the sensor with 1 mg/LSB sensitivity.

It was surprisingly found that the use of a MEMS-based thermal fluid flow sensor (13, 13.1, 13.2) in the spirometer (1) of the invention as claimed, together with an incorporated acceleration sensor (15, 15.1) and a perforated disk (8.1) flow restrictor, provides a remarkably high precision to the inventive spirometer (1) In fact, it renders the device sensitive enough to even measure the minute movements of air moved in or out of the trachea by the heart beat, thus enabling not only full spirometry as intended but also new medical uses which were not available before with prior art spirometers; for instance, high precision full spirometry in connection with the possibility to monitor the heart beat frequency of a patient simultaneously. According to the knowledge of the inventors, such high precisions could not be achieved in the past with prior art portable devices which are evaluating the fluid flow by measuring either a pressure difference before and after a flow restrictor with a known resistance (e.g. using a differential pressure sensor), or by the rotations of a turbine.

In addition, the device may be manufactured easily and at low manufacturing costs, allowing to offer a low-priced, lightweight, energy-efficient, yet highly precise portable electronic spirometer (1), which does not require large and/or heavy energy sources.

In one embodiment, the acceleration sensor (15, 15.1) is further employed for measuring the temperature of the breath; similar to the MEMS-based thermal fluid flow sensor (13, 13.1, 13.2).

In one embodiment, the electronic spirometer (1) further comprises a gyroscope in addition to the acceleration sensor (15, 15.1). The gyroscope detects the horizontal orientation of the spirometer (1) and can be used to detect non-perpendicular orientation of the device during a spirometric measurement manoeuvre. This allows for automatically alerting the user to correct his/her position, and thus for further improved quality of the single manoeuvre as well as the longterm analysis of lung function parameters; in particular, of unsupervised and/or laypersons' spirometry manoeuvres.

In one embodiment, the spirometer (1) further comprises a heart rate sensor (16), a blood oxygen saturation sensor (17; also called pulse oximetry sensor or SpO2 sensor), a temperature sensor for measuring the temperature of the environment (18), an atmospheric pressure sensor (19), and/or a moisture sensor (20; also called humidity sensor). Each of these one or more sensors (16-20) is directly or indirectly connected with the microcontroller (14) such that the microcontroller (14) is capable of receiving a signal from each of the one or more sensors (16-20).

In one embodiment, the heart rate sensor (16) and the blood oxygen saturation (17) are contained within one and the same sensing means, i.e. a combined sensor as depicted e.g. in FIG. 2. In a specific embodiment, this combined sensor operates by reflecting light waves of two distinct wavelengths—usually red (about 600-750 nm) and infrared (about 780 nm-1 mm)—from a vascularized tissue and measuring the remitted light (i.e. reflected or scattered) with a recipient photodiode. Typically, these combined sensors allow two operation modes: SpO2 (red and infrared diodes switched on interchangeably) or heart rate only (only infrared diode switched on). In a more specific embodiment, the combined heart rate and blood oxygen saturation (16, 17) is a MAX30100 module as supplied by Maxim Integrated. The system comprises a red diode, an infrared diode and a photodiode, as well as filtering blocks and digital signal processing units including a I$^2$C (TWI) digital interface. Communication with the sensor allows to control the sampling parameters and current of both light diodes, providing the possibility of dynamically correcting the amplitude of the output signal. Sampling frequencies range within 50 Hz to 1 kHz, corresponding to illuminating times of the diodes from 200 µs to 1600 µs.

Optionally, the blood oxygen saturation (17)—or the combined heart rate and blood oxygen saturation (16, 17)—is housed in the spirometer's (1) main body (9) in such a way that the user's fingers naturally cover the blood oxygen saturation (17) while holding the spirometer (1) in hand during the inhalation and/or exhalation manoeuvres, as is depicted in FIG. 2.

In one embodiment, the spirometer (1) comprises all three environmental sensors, namely the temperature sensor, the atmospheric pressure sensor and the moisture sensor (18-20). In a more specific embodiment, one or all of these environmental sensors (18-20) are supplied with 3.3 V and communicate with the microcontroller (14) via a common I$^2$C bus.

In one embodiment, the temperature sensor (18) and the humidity sensor (20) are contained within one and the same sensing means; i.e. a combined sensor as depicted in FIG. 4. In a specific embodiment, the combined sensor is a digital sensor SHT21D (version 3) as supplied by Sensirion which allows sampling frequencies up to 2 Hz with 12-bit measurement resolution.

In one embodiment, the atmospheric pressure sensor (19) is selected from any sensor capable of measuring pressures in at least the range of about 800 hPa to about 1100 hPa, or about 0.8 bar to about 1.1 bar; preferably sensors which are especially designed for mobile applications, such as piezoresistive pressure sensors. In a specific embodiment, the atmospheric pressure sensor (19) is a digital BMP280 sensor as supplied by Bosch.

The positioning of the three environmental sensors (18, 19, 20) on the main board (27) is depicted in FIG. 4. These environmental sensors (18, 19, 20) may be used e.g. for the BTPS conversion of FVC measurements (BTPS: body temperature pressure saturated); i.e. the vital capacity at maximally forced expiratory effort, expressed in litres at body temperature and ambient pressure saturated with water vapour, as required by the ATS standards of spirometry in order to allow for comparability across different temperatures, pressures and humidity conditions; i.e. a standardisation of environmental conditions (see e.g. "Standardisation of spirometry"; Eur Respir J 2005; 26: 319-338).

In one embodiment, the microcontroller (14) is provided in the form of a so-called System-on-Chip (SoC) unit on a printed circuit board (PCB) as depicted in FIG. 4, also referred to as the main board (27). In a specific embodiment, the microcontroller (14) is a nRF51822-QFAC (rev. 3) SoC-unit as obtainable from Nordic Semiconductor and supplied with an ARM Cortex-M0 core which comprising a BLE radio module, a built-in 256 kB flash memory and 32 kB RAM.

In one embodiment, the spirometer (1) further comprises a communication means, preferably a wireless communication means, and more preferably a radio communication means (21) in order to connect the spirometer (1) to a user's personal computer and/or smartphone or any other computing unit which is adapted to collect, store, analyse, exchange and/or display data. The communication means is employed for the exchange of data related to the fluid flow generated by the spirometer (1), preferably by the microcontroller (14) of the spirometer (1).

The wireless or in particular radio connection can be operative during the measurements, thereby allowing real time display of the measured date. Alternatively, the spirometer (1) may be connected to the user's personal computer and/or his smartphone at a later time point to transfer, or copy, any measured and stored data from the spirometer (1) to the computer and/or smartphone. In a specific embodiment, the radio communication means (21) is a Bluetooth connectivity (21.1), e.g. a Bluetooth 4.0 connectivity. In a further specific embodiment, the radio communication means (21) is a so-called Near Field Communication (NFC) means (21.2) or a Wireless Local Area Network (WLAN) means (21.3). Optionally, different types of radio communication means (21) may be combined in a device, e.g. a Bluetooth connectivity (21.1) together with an NFC means (21.2), as depicted on the main board (27) of FIG. 4.

Measured parameters are digitalized and then wirelessly transmitted to the user's personal computer and/or smartphone or any other computing unit which is adapted to collect, store, analyse, exchange and/or display data, optionally via one or more remote data servers, also called 'cloud'. With regard to the cloud it should be understood, that unlike other prior art devices, the spirometer (1) of the invention may also use a cloud, but does not require it for the device to be operable, to perform the measurement(s) and/or to obtain the result; all computing is done locally on the smartphone.

Further alternatively, or in addition to the radio communication means (21, 21.1, 21.2, 21.3), the spirometer (1) may further comprise a cable communication means (22) via a serial bus, such as a USB connection (22.1).

Both these communication means (wireless or using a cable connection) may further be employed for firmware updates.

In one embodiment, the spirometer (1) further comprises a RAM (random-access memory) and a flash memory in order to store measured data.

As mentioned, the spirometer (1) may be connected to a user's personal computer and/or his smartphone, for analysis, visualisation and also storage of the measured spirometry data; preferably via a dedicated spirometer application ('app') using a proprietary and predictive medical algorithm; or as an 'add-on' integrated in other existing healthcare apps available for iOS or android phones, such as GoogleFit, HealthKit, CareKit or the like (i.e. apps intended as personal and central data collection points for connected third-party electronic accessories for medical and general fitness purposes, where users can e.g. create a medical ID with important medical details).

The dedicated proprietary app is employed to receive signals from the spirometer (1), measure and analyse results in real-time, display the appropriate parameters, store past results, provide diagnostic support, generate printable files (e.g. PDF) for keeping a paper/computer format log, and optionally to send results to physicians. With the help of the portable electronic spirometer (1) and the related app, users can thus track their personal respiratory parameters, as well as the responsiveness to and adequacy of medication, in a far more close-meshed manner than achievable in e.g. hospital settings.

In one embodiment, the collected data (up to 1,000,000 results) from the spirometer (1) are stored in the form of a logged history in the local, internal database of the app such that the data are readily available for the user even when he/she is offline. In case a user uninstalls the application, the database is also removed; however, Android's backup and iOS's CloudKit services allows users to copy persistent application data to remote cloud storage in order to provide a restore point for the application data and settings. When performing a factory reset or converting to a new device, the system automatically restores backup data when the app is re-installed, such that users don't need to reproduce their previous data or settings. Alternatively, or in addition to the local storage, cloud storage may be provided as an 'opt-in' option for the user.

Optionally, the data measured and collected with the spirometer (1) may further be combined with geographical data and data of multiple users then analysed collectively on a remote server in order to create maps of specific changes in conditions in a given area and time for e.g. asthmatic users or allergy sufferers. The data collected via such geolocation provides a framework for building analytical knowledge, correlating data to a certain area, and—where considered expedient—for providing this knowledge to users and/or doctors in a given area, e.g. in the form of alerts on upcoming acute exacerbations and/or increased allergy risks sent to their personal computers and/or smartphones. This optional functionality will be provided for and to users in an anonymised fashion.

The spirometer (1) may further provide motivational messages to users in order to coach them for self-management. It can also provide instant feedback to the user while performing the spirometry measurement (e.g. audible or visual) which allows instructing and/or prompting a user to conduct a desired spirometric breath manoeuvre, such as rapidly exhaling at the right moment. This is believed to be unique for spirometers as other marketed spirometers do not do coach users on how to correctly perform spirometry during the actual measurement, or breath manoeuvre, and/or what to improve in the next manoeuvre. This feedback and/or motivational means facilitates in particular unsupervised use.

In addition, based on data mining and machine learning algorithms comprised in the dedicated app, the spirometer (1) can identify clinical and also environmental patterns (such as temperature, pressure and ambient air humidity) that may be associated with e.g. an upcoming asthma attack and/or a disease progression in a predictive manner. Ultimately, users are thus enabled to eliminate or at least reduce severe hospitalizations due to acute and chronic exacerbations. However, as mentioned, the examination of respiratory parameters may also be helpful for athletes monitoring their training progress or for smokers monitoring the benefits of smoking cessation.

In one embodiment, the spirometer (1) is operated with a long-life battery, such as a lithium-ion polymer (LiPo) battery or a lithium-ion (LiOn) battery. LiPo batteries offer high capacity compared to their small size, and high-speed charging. In a specific embodiment, the battery is a (re) chargeable 3.7V/300 mAh LiPo battery; for instance, an LP-402933-IS-3 battery featuring a built-in NTC 10 kohm thermistor and a transistor protection against overloading. A low-dropout (LDO) type voltage stabiliser then supplies continuous current of 150 mA and a DC output voltage of 3.3 V when the spirometer (1) is switched on, for instance to the microcontroller (14) and all sensors (13, 15-20). In a specific embodiment, the voltage stabiliser is a TPS706 unit as supplied by Texas Instruments. In addition, a voltage divider may be employed if the voltage directed to certain components of the spirometer (1) cannot exceed specific values; e.g. the voltage sampled by the microcontroller (14) not exceeding 1.2 V.

In one embodiment, the battery is charged via an inductive NFC charging system and/or via a USB or mini-USB connector (22.1). In a specific embodiment, the basic component of the wireless charging module is a 5 W unit (BQ51050B) as supplied by Texas Instruments, charging to the maximum voltage of 4.2 V. A reception coil (Wurth Elektronik coil 760308103205) is connected to the unit with inductiveness of 11 µH. The unit comprises a LiPo and LiOn battery charger with the function of monitoring temperature using an NTC thermistor (10 kohm). It also provides the possibility of selecting a priority for the source of charging; for example, if USB charging is available via a connected mini-USB port, the charging unit will stop wireless charging and switch to USB-charging. In a further specific embodiment, the basic component for the charging module is a BQ24040-unit as supplied by Texas Instruments, a LiPo and LiOn battery charger charging to the voltage of 4.2 V. Maximum charging current is 800 mA, and maximum initial charging by default amounts to 300 mA for devices with a 300 mAh battery, such as the battery used in one embodiment of the spirometer (1).

The module which is responsible for detecting the charging source (e.g. wireless vs. USB) also performs the task of automatically starting the spirometer (1) during charging, as is necessary in order to inform the user about the charging status by means of the LEDs (23.1); i.e. the user does not have to start the spirometer (1) manually via ON/OFF button (25) in order to see the charging status. The microcontroller (14) uses the module to check the charging source and status, and this information may also be provided to the user via the app. After charging is completed, the device will be switched off automatically.

In one embodiment, the spirometer's (1) main body (9) is further equipped with optical (23) and/or acoustical (24) signalling means providing use-related information such as ON/OFF-status, battery status and the like to the user. In a specific embodiment, the spirometer's (1) main body (9) is fitted with light emitting diodes (LEDs), for instance a set of blue LEDs (23.1) arranged at the top of the main body (9) as depicted in FIG. 2. The LEDs display specific status information, such as device start-up, data transfer, low battery (e.g. all diodes flashing) or battery charging status (e.g. diodes illuminating subsequently).

In a more specific embodiment, the direct control of these LEDs is provided by a TLC59108 unit. Each diode consumes only about 5 mA of current (depending on the light intensity) while the microcontroller (14) is able to supply a maximum of about 120 mA. The microcontroller (14) also enables to set the brightness of illumination using a built-in PWM module (pulse-width modulation), as well as to set the mode of diode flashing with particular frequency and duration of illumination on/off-time.

In one embodiment, the spirometer (1) exhibits a mean energy consumption, or current consumption, during its operation that is not higher than about 90 mA in total. Preferably, the mean energy consumption does not exceed about 50 mA, even with all light emitting diodes (LEDs) being illuminated. On average, the spirometer (1) equipped with a freshly charged 300 mAh battery is operable for about 120 days in stand-by mode, for about 56 days for single users and for about 5.6 days when used for multiple patients in e.g. a doctor's office. The time estimated for continuous, uninterrupted operation on one battery charge is about 6 h. In other words, the inventive spirometer (1) is not only allowing for spirometric measurements at a remarkably high precision but is highly energy-efficient at the same time, thereby reducing the need for expensive and heavy energy sources.

The spirometer's (1) main components which get in contact with the user's skin, namely the tubular mouthpiece (2) and the main body (9), may be prepared from any biocompatible material, including biocompatible polymers. In one embodiment, biocompatible Polyjet photopolymer (MED610) is employed, a rigid medical material suited for prolonged skin contact of more than 30 days and short-term mucosal membrane contact of up to 24 hours, but also suited for rapid prototyping. MED610 features high dimensional stability and colorless transparency. Also polycarbonate-ISO (PC-ISO) may be employed; a high strength thermoplastic material which in its pure form is biocompatible and sterilizable by gamma irradiation or ethylene oxide (sterilization method ET0). PC-ISO is commonly used for packaging medicines and in the manufacture of medical devices.

As mentioned earlier, the front end of the tubular mouthpiece, i.e. the end comprising the proximal opening may optionally be configured as a detachable part of the tubular mouthpiece, thereby allowing to remove this front end portion of the mouthpiece; for instance, to clean it, or to discard and replace it, after contact with a user's lips and/or tongue. In case of such disposable front end portions (or other disposable parts as needed in multi-patient settings), the materials may also include more simple biocompatible materials such as cardboard. Alternatively, or in addition, the detachable front end portion of the mouthpiece may be equipped with one or more filters to remove airborne particles, saliva droplets and/or bacteria; thereby further reducing the risk of contaminating the sensitive MEMS-based thermal fluid flow sensor (13, 13.1, 13.2). Such filter-mouthpieces are available at low cost and thus may be replaced for each patient in multi-patient settings.

Further optionally the spirometer may be provided to the user together with a nose-clip, such as to allow the user to block the nose while performing spirometric measurements. In one embodiment, the nose-clip and the spirometer are provided as a kit, optionally further comprising readable instructions on the correct use of the spirometer and/or the nose-clip.

In a second aspect, the invention provides a method for measuring a health parameter of a human subject selected from
a) a forced vital capacity (FVC),
b) a forced expiratory volume (FEV) such as the forced expiratory volume in 1 second (FEV1),
c) a peak expiratory flow (PEF)
d) a forced expiratory flow (FEF) such as the forced expiratory flow at 25%-75% of FVC (FEF25-75),
e) a maximum voluntary ventilation (MVV),
f) a mean expiratory flow,
g) a slow vital capacity (SVC),
h) a functional residual capacity (FRC),
i) an expiratory reserve volume (ERV),
j) a maximum speed of expiration,
k) a forced inspiratory volume (FIV) such as the forced inspiratory volume in 1 second (FIV1),
l) a forced inspiratory vital capacity (FIVC),
m) a peak inspiratory flow (PIF),
or any combination of these (e.g. an inspiratory Tiffeneau value: FIV1/FIVC), the method comprising a step of the human subject performing a breathing manoeuvre through the portable electronic spirometer (1) as described above. The actual breathing manoeuvres are the same as performed with prior art spirometers; the specifics will depend on the actual lung function parameter to be determined. Examples may be found in the "Standardisation of spirometry" e.g. as published e.g. by the American Thoracic Society (ATS) or the European Respiratory Society (ERS) (see Eur Respir J 2005; 26: 319-338) or the ISO 26782:2009 (specifying requirements for spirometers intended for the assessment of pulmonary function in humans weighing more than 10 kg).

Beyond full spirometry, the spirometer (1) offers further potential applications, or uses, in various clinical scenarios. For instance, the spirometer (1) may be used for the differential diagnosis of dyspnoea; i.e. the device allows differentiating between cardiac vs. respiratory dyspnoea. When patients are admitted to emergency departments due to chest pain and dyspnoea, this is commonly caused by either coronary insufficiency (ischemia), heart failure (lung congestion) or bronchial obstruction (COPD). Commonly, a differential diagnosis is hindered by the significant overlap of about 30% of ischemic heart disease (coronary artery disease) patients and COPD patients. The spirometer (1) allows to understand if there is a significant obstruction, in which case the spirometric parameters would not be ok. Hence, if the spirometric parameters are ok, while the cardiac parameters are not, the chest pain and further symptoms are most likely of a cardiac origin, while in the vice versa case, the symptoms are most likely caused bronchially. If both, the respiratory and the cardiac parameters are not ok, the chest pain and dyspnea are caused by a combination of either coronary insufficiency (ischemia), heart failure (lung congestion) or bronchial obstruction (COPD).

In that aspect, it should be understood that this type of differential diagnosis would be possible with prior art devices, too; however, the desktop spirometers as commonly found in hospitals are usually rather large and require longer set-up times. The small hand-held spirometer (1) in contrast is far more practical and requires shorter set-up times, rendering it more suitable for use in emergency and/or intensive care units.

Furthermore, the spirometer (1) may be used in hospitals during pre-extubation assessment of respiratory patients which is one crucial element to prevent failed extubations. The spirometer (1) may be used to determine the efficacy of spontaneous breathing of an intubated patient by either applying the flow sensor (13, 13.1, 13.2) directly on the intubation tube and/or by coupling the spirometer (1) with the intubation tube, such as to measure the fluid flow caused by spontaneous breathing while the ventilator is switched off.

Also, evaluation of cardiac arrest patient requires assessment of the electrical activity as well as the haemodynamic function of the heart, the latter usually being evaluated using pulse. However, in patients with peripheral artery disease and/or those with severe peripheral oedema it may be difficult to feel the pulse despite good haemodynamic function of the heart. The spirometer (1) allows to indirectly evaluate the contractions of the heart by sensing the very discreet movements of air in the lungs and trachea which is caused by the heart beats.

In a third aspect, the invention provides a system comprising:
- the portable electronic spirometer (1) according to the first aspect of the invention, and
- a first air quality measurement device comprising communication means adapted for data exchange with the portable electronic spirometer (1) and/or with a separate computing unit, and equipped with one or more air quality sensors, preferably selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors, for determining determine the air quality at the location of the first air quality measurement device, and optionally
- a separate computing unit adapted to collect and analyse at least the data obtained from the spirometer (1) according to the first aspect of the invention and from the first air quality measurement device.

Air pollution is known to be linked to a decrease in lung function in healthy adults and children, and to adversely impact different acute and chronic pulmonary diseases, such as asthma, chronic obstructive pulmonary disease (COPD), bronchitis and cystic fibrosis (CF). Air pollution can trigger cellular responses in the lung, resulting in cytotoxicity, inflammation, and mutagenesis. Bronchial epithelial cells from patients suffering from pulmonary diseases are highly sensitive to airborne particulate matter-induced oxidative stress and apoptosis at a much lower dose than healthy bronchial cells. Hence, an intense response to the oxidative stress induced by air pollution remains the base for disease progression and exacerbations. This pathomechanism was confirmed in observational studies which showed that the annual average levels of air pollution exposure were associated with lung function decrease and an increased likelihood of exacerbation. Pulmonary exacerbations contribute significantly to the burden of disease, with a negative impact on lung function, quality of life, health system costs.

Especially, particulate matter (PM), pollen, ozone ($O_3$), nitrogen dioxide ($NO_2$), sulfur dioxide ($SO_2$) and carbon monoxide (CO) have been identified as key pollutants impairing health. For instance, there is a close quantitative relationship between increased mortality or morbidity (both daily and over time) and the exposure to high concentrations of inhalable coarse particles (2.5-10 μm; PM10), and inhalable fine particles (≤2.5 μm; PM2.5). In fact, PM10 and PM2.5 pollution have health impacts even at very low concentrations; in fact, no threshold has been identified below which no health damage is observed. Therefore, guidelines such as by the World Health Organization (WHO) aim to achieve the lowest possible PM-concentration and advise annual means of max. 10 $\mu g/m^3$ (PM2.5) or 20 $\mu g/m^3$ (PM10), and 24-hour means of max. 25 $\mu g/m^3$ (PM2.5) or 50 $\mu g/m^3$ (PM10).

Also, excessive ozone ($O_3$) in the air can have a marked effect on human health. It can cause breathing problems, trigger asthma, reduce lung function and cause lung diseases. In Europe, it is currently one of the air pollutants of most concern. Several European studies have reported that the daily mortality rises by 0.3% and that for heart diseases by 0.4%, per 10 $\mu g/m^3$ increase in ozone exposure. An 8-hour mean of max. 100 $\mu g/m^3$ is advised by the guidelines.

Epidemiological studies have shown that symptoms of bronchitis in asthmatic children increased in association with long-term exposure to nitrogen dioxide ($NO_2$). At short-term concentrations exceeding 200 $\mu g/m^3$, it is even toxic, causing significant inflammation of the airways. A 1-hour mean of max. 200 $\mu g/m^3$ is advised by the guidelines.

Sulfur dioxide ($SO_2$) can affect the respiratory system and lung function, causing inflammation of the respiratory tract and resulting in coughing, increased mucus secretion, aggravation of asthma and chronic bronchitis and an increased risk of respiratory tract infections. Studies indicate that exposure periods as short as 10 minutes already increase the proportion of asthma patients experiencing changes in pulmonary function and respiratory symptoms. Asthmatic subjects exercising in $SO_2$-polluted air develop bronchoconstriction within minutes, even at levels as low as 0.25 ppm. Lung function parameters such as FEV1 were decreased in response to exposure to only 0.4 to 1.0 ppm $SO_2$. Furthermore, hospital admissions due to cardiac disease and mortality are increased on days with $SO_2$ levels above the recommended 24-hour mean of max. 20 μg/m3 or the recommended 10-minute mean of max. 500 $\mu g/m^3$.

Carbon monoxide (CO) remains the second most strongly correlated air pollutant causing asthma hospital admissions.

The first air quality measurement device is used to generate data related to the air quality (or lack thereof), for instance, the nature and/or the extent of air pollutants (ozone, pollen, particulate matter, etc.) present at any given time at the location of the first air quality measurement device, such as inside the home of the subject using the spirometer (1).

For this purpose, the first air quality measurement device comprises one or more sensors selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors. These sensors may be provided separately (in other words, one sensor for each measurand). Alternatively, the sensors may be combined such as to use one sensor for a plurality of measurands. Exemplary and non-limiting embodiments of these sensors will be described below.

In one embodiment, the humidity sensor, the temperature sensor and the pressure sensor may be provided in combined form. In a specific embodiment, the sensor is a Bosch® BME280 sensor, a small (2.5×2.5×0.93 mm), high performance combined, digital humidity-, pressure, -and temperature sensor with a low power consumption. The humidity sensor provides an extremely fast response time and high overall accuracy over a wide temperature range. The pressure sensor is an absolute barometric pressure sensor with extremely high accuracy and resolution and drastically lower noise. The integrated temperature sensor has been optimized for lowest noise and highest resolution. Its output is used for temperature compensation of the pressure and humidity sensors and can also be used for estimation of the ambient temperature.

In one embodiment, the MOS-type gas sensor is a FIGARO® TGS8100 air quality sensor comprising a sensing chip with a metal-oxide semiconductor (MOS) layer and an integrated heater on a silicon substrate. The sensor is housed in a standard surface-mount ceramic package and requires a heater power consumption of only 15 mW. In the presence of detectable gases (such as hydrogen, ethanol, carbon monoxide (CO), isobutane, methane, cigarette smoke, kitchen odors, or the like), the sensor conductivity increases depending on gas concentration in the air. A simple electrical circuit can convert the change in conductivity to an output signal which corresponds to the gas concentration.

In one embodiment, the airborne-particles sensor is a Sharp® GP2Y1030AU0F, a high sensitivity airborne-particles sensor (also called dust sensor) operating with a built-in microcomputer and an optical sensing system that can detect e.g. particulate matter like PM2.5 and PM10. An infrared emitting diode (IRED) and a phototransistor are diagonally arranged in the sensor to detect the light reflected by airborne particles such as dust and/or cigarette smoke with the sensor being able to distinguish these two by a pulsed pattern of output voltage.

In one embodiment, the ozone ($O_3$) sensor is a small-sized (15×15×3 mm), printed ozone sensor, such as the 3SP-O3-20 sensor by SPEC sensors.

In one embodiment, the nitrogen dioxide ($NO_2$) sensor is an electrochemical sensor, such as the Figfaro FECS42-20 sensor.

In one embodiment, the sulfur dioxide ($SO_2$) sensor is an amperometric gas sensor, also provided by SPEC sensors; i.e. an electrochemical sensor which generates a current at a working (or sensing) electrode that is proportional to the volumetric fraction of the $SO_2$ gas. Besides the working (or sensing) electrode and its counter-electrode, the sensor comprises a reference electrode to improve stability, signal-to-noise ratio, and response time.

In one of the preferred embodiments, the first air quality measurement device is not only responsible for generating data related to the air quality via its inbuilt sensors but further serves as a charging dock, or docking station, for at least the portable electronic spirometer (1), preferably a Near Field Communication (NFC) charging dock. Like this, the spirometer (1) only needs to be placed on top of the first air quality measurement device to recharge; for instance, over night.

Besides the sensors for determining air quality, the first air quality measurement device further comprises a microcontroller and a communication means, preferably a wireless communication means, and further preferably a Bluetooth connectivity, such as Bluetooth 4.0. In a specific embodiment, the microcontroller is a nRF51422-CEAA as produced by Nordic Semiconductor, comprising a 32-bit ARM® Cortex™ M0 central processing unit (CPU) with 256 kB flash and 32 kB RAM as well as an embedded 2.4 GHz transceiver. The microcontroller allows for both Bluetooth® low energy (BLE; previously called Bluetooth Smart) and ANT™ wireless connectivities. A ceramic antenna for Bluetooth 2.4 GHz is used for improved reception and more stable connection.

As mentioned, the separate computing unit is adapted to collect and analyse at least the data obtained from the spirometer (1) and from the first air quality measurement device. The purpose of the separate computing unit is to allow for comparison and/or correlation of the data obtained from the spirometer (1) with the data obtained from the first air quality measurement device (and optionally further data), in order to obtain a deeper insight into e.g. the pathogenesis of respiratory diseases; for instance, to correlate days of poorer results in spirometric lung performance tests run by the spirometer (1) with the air quality data measured by the first air quality measurement device on such days.

For this purpose, the separate computing unit in one embodiment comprises a communication means coupled with a microcontroller for performing data collection and data analysis (e.g. a microcontroller in the form of a so-called System-on-Chip (SoC) unit on a printed circuit board (PCB)); and data storage means (e.g. a random-access memory (RAM) and/or a flash memory) in order to store collected and/or analysed data obtained from at least the spirometer (1) and the first air quality measurement device (hereafter shortly referred to as 'spirometer data' and 'first air quality data', respectively), and optionally further data.

Furthermore, the separate computing unit typically comprises an interface that is adapted to communicate with a user of the inventive system (e.g. the user of the spirometer (1), his/her physician or caretakers), and to provide information to the user on any of the 'spirometer data' and 'first air quality data' as well as information obtained from comparing and/or correlating the 'spirometer data' and 'first air quality data'. In one embodiment, this interface is a visual display.

In one embodiment, the separate computing unit comprises a wireless communication means, preferably a radio communication means; e.g. a Bluetooth connectivity or a Near Field Communication (NFC) means.

In one embodiment, the separate computing unit is a personal computer (including laptops and handheld PCs) and/or smartphone.

In a further embodiment, the system may comprise two or more separate computing units, optionally in the form of personal computers (including laptops and handheld PCs) and/or smartphones.

In one embodiment, the separate computing unit is further communicatively coupled to one or more remote data servers. Said remote servers may be employed to store and analyse the 'spirometer data' and 'first air quality data', information obtained from comparing and/or correlating the 'spirometer data' and 'first air quality data', and optionally further data.

In one of the preferred embodiments, a proprietary software application ('app') is provided on the separate computing unit and/or the remote date servers for performing the comparison and/or correlation of at least the 'spirometer data' and 'first air quality data'. In a specific embodiment, the app may also be programmed to perform further tasks such as displaying the 'spirometer data', the 'first air quality data' and/or information obtained from their comparison and/or correlation to a user of the inventive system (e.g. as graphical interpretations of the data via interface(s) of the one or more computing units); monitoring said data and information as well as a user's medication over the course of time; creating printable file formats of any data analysis results; send reminders or warning notice to the user (e.g. related to medication time points, smog-warnings, etc.); and/or sharing information with health care providers such as physicians, care givers, health care organisations and/or other users of the 'app' (optionally in anonymised form).

Optionally, the system as described above further comprises a nose-clip, such as to allow the user to block the nose while performing spirometric measurements. Further optionally, the system further comprises readable instructions on the correct use of the spirometer and/or the nose-clip.

In one embodiment, the system as described above further comprises a second air quality measurement device adapted for data exchange with the portable electronic spirometer (1) and/or with a separate computing unit, and equipped with one or more air quality sensors, preferably selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors, in order to determine the air quality at the location of the second air quality measurement device. This second air quality measurement device may be used in addition to the first air quality measurement device, or optionally instead of the first (e.g. when travelling). With respect to the selected sensors, the same provisions may apply as described for the first air quality measurement device described above.

Unlike the first air quality measurement device which is typically more stationary (for instance, set up in the home of the user), the second air quality measurement device may be more easily portable in that it is even smaller and more compact than the first device. For instance, the second air quality measurement device may have a size which allows e.g. attachment to a keychain whereas the first air quality measurement device may have a size and shape resembling an external hard drive (e.g. about 7-17 cm long and about 4-8 cm wide). Like this, the second air quality measurement device may e.g. be used when travelling, or the device may be used at work, in the car or any other place of interest, where the subject using the spirometer (1) wants to determine the air quality. It is also possible to place the second air quality measurement device outside.

In one embodiment, the separate computing unit of the system as described above also collects and analyses the data obtained from the second air quality measurement device. In this case, the data obtained from the second air quality measurement device (shortly, the 'second air quality data') may be treated in the same way as the data obtained from the first device; e.g. compared and/or correlated with the 'spirometer data'.

In one embodiment, the separate computing unit further allows for the geolocalisation of at least the air quality data obtained from the first air quality measurement device, and optionally of the air quality data obtained from the second air quality measurement device. The geolocalisation functionality may be provided for all users, preferably in anonymous form such as to retain the privacy of each user. Based on this functionality, the inventive system may be able to, for instance, provide warnings to a user (e.g. on smog, pollen and/or other allergens which may impact their lung functions and/or respiratory health), and/or to create geographic maps of all users along with the changes in their respective lung function and/or respiratory health condition at any given time. The data collected through geolocalisation may thus provide a framework for building an even further analytical knowledge of the data provided, e.g. the correlation to a certain area, to specific weather phenomena, etc.

This means, by using the system according to the third aspect of the invention, the method according to the second aspect of the invention may be complemented with additional data such as data related to the air quality (pollutants, ozone, etc.) and/or geolocation data, thereby allowing to correlate the health parameter of the human subject (such as FVC, FEV or PEF) with these additional data.

In other words, in a fourth aspect the invention provides a method for measuring one or more health parameters of a human subject selected from (a) a forced vital capacity (FVC), (b) a forced expiratory volume (FEV) such as the forced expiratory volume in 1 second (FEV1), (c) a peak expiratory flow (PEF), (d) a forced expiratory flow (FEF), such as the forced expiratory flow at 25%-75% of the FVC (FEF25-75), (e) a maximum voluntary ventilation (MVV), (f) a mean expiratory flow, (g) a slow vital capacity (SVC), (h) a functional residual capacity (FRC), (i) an expiratory reserve volume (ERV), (j) a maximum speed of expiration, (k) a forced inspiratory volume (FIV) such as the forced inspiratory volume in 1 second (FIV1), (l) a forced inspiratory vital capacity (FIVC), (m) a peak inspiratory flow (PIF), or any combination of these (e.g. an inspiratory Tiffeneau value: FIV1/FIVC), the method comprising a step of the human subject performing a breathing manoeuvre through the spirometer (1) as described above as the first aspect of the invention; wherein the one or more health parameters are correlated with air quality data, and optionally geolocalisation data, derived from the system as described above as the third aspect of the invention.

The invention claimed is:
1. A portable electronic spirometer comprising:
(a) a tubular mouthpiece with
  a proximal opening for insertion into the mouth of a user,
  a distal opening,
  a main fluid channel extending between the proximal opening and the distal opening,
  a first lateral opening,
  a second lateral opening positioned at a longitudinal distance to the first lateral opening, and
  a flow restrictor positioned in the main fluid channel between the first and the second lateral opening; and
(b) a main body with
  a first fluid opening connectible with the first lateral opening of the mouthpiece,
  a second fluid opening connectible with the second lateral opening of the mouthpiece,
  a bypass fluid channel extending between the first and the second fluid opening,
  a MEMS-based thermal fluid flow sensor positioned at the bypass fluid channel for generating a signal in response to the fluid flow in the bypass fluid channel, and
  a microcontroller connected with the fluid flow sensor for calculating the fluid flow from the signal generated by the flow sensor;
  wherein the distance between the flow restrictor and the first lateral opening along the longitudinal axis of the main fluid channel is from about 5 mm to about 15 mm; and the distance between the flow restrictor and the second lateral opening from about 25 mm to about 45 mm.

2. A method for measuring a health parameter of a human subject selected from:
(a) a forced vital capacity,
(b) a forced expiratory volume,
(c) a peak expiratory flow,
(d) a forced expiratory flow (FEF),
(e) a maximum voluntary ventilation (MVV),
(f) a mean expiratory flow,
(g) a slow vital capacity (SVC),
(h) a functional residual capacity (FRC),
(i) an expiratory reserve volume (ERV),
(j) a maximum speed of expiration,
(k) a forced inspiratory volume (FIV),
(l) a forced inspiratory vital capacity (FIVC),
(m) a peak inspiratory flow (PIF),
or any combination of these, the method comprising a step of the human subject performing a breathing manoeuvre through the spirometer of claim 1.

3. The method of claim 2, wherein the one or more health parameter obtained with the spirometer is correlated with air quality data, and optionally geolocalisation data.

4. A method for measuring one or more health parameters of a human subject selected from
   a) a forced vital capacity (FVC),
   b) a forced expiratory volume (FEV),
   c) a peak expiratory flow (PEF),
   d) a forced expiratory flow (FEF),
   e) a maximum voluntary ventilation (MVV),
   f) a mean expiratory flow,
   g) a slow vital capacity (SVC),
   h) a functional residual capacity (FRC),
   i) an expiratory reserve volume (ERV),
   j) a maximum speed of expiration,
   k) a forced inspiratory volume (FIV),
   l) a forced inspiratory vital capacity (FIVC),
   m) a peak inspiratory flow (PIF),
or any combination of these, the method comprising a step of the human subject performing a breathing manoeuvre through the spirometer of claim 1,
wherein the one or more health parameters are correlated with air quality data, derived from a system comprising:
   a portable electronic spirometer comprising:
(a) a tubular mouthpiece with
   a proximal opening for insertion into the mouth of a user,
   a distal opening,
   a main fluid channel extending between the proximal opening and the distal opening,
   a first lateral opening,
   a second lateral opening positioned at a longitudinal distance to the first lateral opening, and
   a flow restrictor positioned in the main fluid channel between the first and the second lateral opening; and
(b) a main body with
   a first fluid opening connectible with the first lateral opening of the mouthpiece,
   a second fluid opening connectible with the second lateral opening of the mouthpiece,
   a bypass fluid channel extending between the first and the second fluid opening,
   a MEMS-based thermal fluid flow sensor positioned at the bypass fluid channel for generating a signal in response to the fluid flow in the bypass fluid channel, and
   a microcontroller connected with the fluid flow sensor for calculating the fluid flow from the signal generated by the flow sensor;
   wherein the distance between the flow restrictor and the first lateral opening along the longitudinal axis of the main fluid channel is from about 5 mm to about 15 mm; and the distance between the flow restrictor and the second lateral opening from about 25 mm to about 45 mm; and
   a first air quality measurement device comprising communication means adapted for data exchange with the portable electronic spirometer and/or with a separate computing unit, and equipped with one or more air quality sensors for determining the air quality at the location of the first air quality measurement device.

5. The method of claim 4, wherein the one or more health parameter obtained with the spirometer is correlated with air quality data, and geolocalisation data derived from the system.

6. The system of claim 4, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

7. A system comprising:
   the portable electronic spirometer of claim 1, and
   a first air quality measurement device comprising communication means adapted for data exchange with the portable electronic spirometer and/or with a separate computing unit, and equipped with one or more air quality sensors for determining the air quality at the location of the first air quality measurement device.

8. The system of claim 7, wherein the first air quality measurement device further serves as a charging dock for at least the portable electronic spirometer.

9. The system of claim 8, wherein charging dock is a Near Field Communication (NFC) charging dock.

10. The system of claim 7, wherein the first air quality measurement device comprises a wireless communication means.

11. The system of claim 7, wherein the system further comprises a second air quality measurement device adapted for data exchange with the portable electronic spirometer and/or with a separate computing unit, and equipped with one or more air quality sensors, in order to determine the air quality at the location of the second air quality measurement device.

12. The system of claim 11, wherein the separate computing unit also collects and analyses the data obtained from the second air quality measurement device.

13. The system of claim 11, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

14. The system of claim 7, further comprising a communication means for the exchange of data related to the fluid flow generated by the spirometer; and
   further comprising a separate computing unit adapted to collect and analyse at least the data obtained from the spirometer and from the first air quality measurement device;
   wherein the separate computing unit further allows for the geolocalisation of at least the air quality data obtained from the first air quality measurement device, and optionally of the air quality data obtained from the second air quality measurement device.

15. The system of claim 7, further comprising a communication means for the exchange of data related to the fluid flow generated by the spirometer; and
   further comprising a separate computing unit adapted to collect and analyse at least the data obtained from said spirometer and from the first air quality measurement device.

16. The system of claim 7, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

17. The portable electronic spirometer of claim 1, wherein the distance between the flow restrictor and the first lateral opening along the longitudinal axis of the main fluid channel is from about 8 mm to about 12 mm.

18. The portable electronic spirometer of claim 1, wherein distance between the flow restrictor and the second lateral opening from about 30 mm to about 40 mm.

19. A portable electronic spirometer comprising:
(a) a tubular mouthpiece with
a proximal opening for insertion into the mouth of a user,
a distal opening,
a main fluid channel extending between the proximal opening and the distal opening,
a first lateral opening,
a second lateral opening positioned at a longitudinal distance to the first lateral opening, and
a flow restrictor positioned in the main fluid channel between the first and the second lateral opening; and
(b) a main body with
a first fluid opening connectible with the first lateral opening of the mouthpiece,
a second fluid opening connectible with the second lateral opening of the mouthpiece,
a bypass fluid channel extending between the first and the second fluid opening,
a MEMS-based thermal fluid flow sensor positioned at the bypass fluid channel for generating a signal in response to the fluid flow in the bypass fluid channel, and
a microcontroller connected with the fluid flow sensor for calculating the fluid flow from the signal generated by the flow sensor;
wherein the MEMS-based thermal fluid flow sensor is a bidirectional flow sensor.

20. The spirometer according to claim 19, further comprising a communication means for the exchange of data related to the fluid flow generated by the spirometer.

21. The spirometer of claim 19, wherein the flow restrictor exhibits a flow resistance in the range from about 0.01 to about 0.2 kPa/(L/s), at a fluid flow of 60 SLM to 900 SLM, optionally wherein the flow restrictor is adapted or configured such as to cause a fluid flow in the bypass fluid channel which is from about 1:10 to about 1:200 of the fluid flow in the main fluid channel, and optionally wherein the flow restrictor is a perforated disk having a cross-sectional orientation with respect to the main fluid channel.

22. The spirometer of claim 21, wherein
the perforated disk exhibits from about 1 to about 100 perforations, and/or
wherein the total combined area of all perforations is from about 26% to about 96% of the cross-sectional area of the main fluid channel at the position of the perforated disk, and
wherein the perforations are optionally circular, elliptic or polygonal; or shaped as sectors of a circle or oval; or exhibit an irregular shape.

23. The spirometer of claim 19, further comprising an acceleration sensor which is different from the MEMS-based thermal fluid flow sensor, optionally wherein the acceleration sensor is a 3-axis sensor with a sensitivity (So) of at least 973 counts/g±5% for each of the three axes.

24. The spirometer of claim 23, wherein the microcontroller is programmed to calculate a corrected fluid flow from the signal generated by the flow sensor and from a signal generated by the acceleration sensor.

25. The spirometer of claim 19, further comprising one or more of the following sensors:
(a) a heart rate sensor,
(b) a blood oxygen saturation sensor,
(c) a temperature sensor for measuring the temperature of the environment,
(d) an atmospheric pressure sensor,
(e) a moisture sensor;

wherein each of the one or more sensors is directly or indirectly connected with the microcontroller such that the microcontroller is capable of receiving a signal from each of the one or more sensors.

26. The spirometer of claim 19, further comprising a Wireless communication means.

27. A system comprising:
the portable electronic spirometer of claim 19, and
a first air quality measurement device comprising communication means adapted for data exchange with the portable electronic spirometer and/or with a separate computing unit, and equipped with one or more air quality sensors for determining the air quality at the location of the first air quality measurement device.

28. The system of claim 27, further comprising a communication means for the exchange of data related to the fluid flow generated by the spirometer; and
further comprising a separate computing unit adapted to collect and analyse at least the data obtained from said spirometer and from the first air quality measurement device.

29. The system of claim 27, wherein the first air quality measurement device further serves as a charging dock for at least the portable electronic spirometer.

30. The system of claim 29, wherein the charging dock is a Near Field Communication (NFC) charging dock.

31. The system of claim 27, wherein the first air quality measurement device comprises a wireless communication means.

32. The system of claim 31, wherein the wireless communication means is a Bluetooth connectivity.

33. The system of claim 27, further comprising a separate computing unit adapted to collect and analyse at least the data obtained from the spirometer and from the first air quality measurement device;
wherein the separate computing unit further allows for the geolocalisation of at least the air quality data obtained from the first air quality measurement device, and optionally of the air quality data obtained from the second air quality measurement device.

34. The system of claim 27, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

35. The portable electronic spirometer of claim 19, wherein the MEMS-based thermal fluid flow sensor is a monolithic CMOS flow sensor comprising a sensor chip, the chip comprising an encapsulated gas bubble, a microheater for heating the gas bubble, a first plurality of thermopiles located on a first side of the gas bubble, and a second plurality of thermopiles located on a second side of the gas bubble which is opposite to the first side.

36. A method for measuring a health parameter of a human subject selected from:
(a) a forced vital capacity,
(b) a forced expiratory volume,
(c) a peak expiratory flow,
(d) a forced expiratory flow (FEF),
(e) a maximum voluntary ventilation (MVV),
(f) a mean expiratory flow,
(g) a slow vital capacity (SVC),
(h) a functional residual capacity (FRC),
(i) an expiratory reserve volume (ERV),
(j) a maximum speed of expiration, (k) a forced inspiratory volume (FIV),
(l) a forced inspiratory vital capacity (FIVC),
(m) a peak inspiratory flow (PIF),
or any combination of these, the method comprising a step of the human subject performing a breathing manoeuvre through the spirometer of claim 19.

37. A method for measuring one or more health parameters of a human subject selected from
   a) a forced vital capacity (FVC),
   b) a forced expiratory volume (FEV),
   c) a peak expiratory flow (PEF),
   d) a forced expiratory flow (FEF),
   e) a maximum voluntary ventilation (MVV),
   f) a mean expiratory flow,
   g) a slow vital capacity (SVC),
   h) a functional residual capacity (FRC),
   i) an expiratory reserve volume (ERV),
   j) a maximum speed of expiration,
   k) a forced inspiratory volume (FIV),
   l) a forced inspiratory vital capacity (FIVC),
   m) a peak inspiratory flow (PIF),
or any combination of these, the method comprising a step of the human subject performing a breathing manoeuvre through the spirometer of claim 19;
wherein the one or more health parameters are correlated with air quality data derived from a system comprising:
   a portable electronic spirometer comprising:
   (a) a tubular mouthpiece with
      a proximal opening for insertion into the mouth of a user,
      a distal opening,
      a main fluid channel extending between the proximal opening and the distal opening,
      a first lateral opening,
      a second lateral opening positioned at a longitudinal distance to the first lateral opening, and
      a flow restrictor positioned in the main fluid channel between the first and the second lateral opening; and
   (b) a main body with
      a first fluid opening connectible with the first lateral opening of the mouthpiece,
      a second fluid opening connectible with the second lateral opening of the mouthpiece,
      a bypass fluid channel extending between the first and the second fluid opening,
      a MEMS-based thermal fluid flow sensor positioned at the bypass fluid channel for generating a signal in response to the fluid flow in the bypass fluid channel, and
      a microcontroller connected with the fluid flow sensor for calculating the fluid flow from the signal generated by the flow sensor;
      wherein the MEMS-based thermal fluid flow sensor is a bidirectional flow sensor; and
   a first air quality measurement device comprising communication means adapted for data exchange with the portable electronic spirometer and/or with a separate computing unit, and equipped with one or more air quality sensors for determining the air quality at the location of the first air quality measurement device.

38. The system of claim 37, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

39. The method of claim 37, wherein the one or more health parameter obtained with the spirometer is correlated with air quality data, and geolocalisation data derived from the system.

40. The spirometer according to claim 19, further comprising a communication means for the exchange of data related to the fluid flow generated by the spirometer by the microcontroller of the spirometer.

41. A portable electronic spirometer comprising:
   (a) a tubular mouthpiece with
      a proximal opening for insertion into the mouth of a user,
      a distal opening,
      a main fluid channel extending between the proximal opening and the distal opening,
      a first lateral opening,
      a second lateral opening positioned at a longitudinal distance to the first lateral opening, and
      a flow restrictor positioned in the main fluid channel between the first and the second lateral opening; and
   (b) a main body with
      a first fluid opening connectible with the first lateral opening of the mouthpiece,
      a second fluid opening connectible with the second lateral opening of the mouthpiece,
      a bypass fluid channel extending between the first and the second fluid opening,
      a MEMS-based thermal fluid flow sensor positioned at the bypass fluid channel for generating a signal in response to the fluid flow in the bypass fluid channel, and
      a microcontroller connected with the fluid flow sensor for calculating the fluid flow from the signal generated by the flow sensor;
      wherein the mean Energy consumption of the device during its operation is not higher than about 90 mA in total.

42. The portable electronic spirometer of claim 41, wherein the mean Energy consumption of the device during its operation is not higher than about 50 mA.

43. A system comprising:
   a portable electronic spirometer comprising:
   (a) a tubular mouthpiece with
      a proximal opening for insertion into the mouth of a user,
      a distal opening,
      a main fluid channel extending between the proximal opening and the distal opening,
      a first lateral opening,
      a second lateral opening positioned at a longitudinal distance to the first lateral opening, and
      a flow restrictor positioned in the main fluid channel between the first and the second lateral opening; and
   (b) a main body with
      a first fluid opening connectible with the first lateral opening of the mouthpiece,
      a second fluid opening connectible with the second lateral opening of the mouthpiece,
      a bypass fluid channel extending between the first and the second fluid opening,
      a MEMS-based thermal fluid flow sensor positioned at the bypass fluid channel for generating a signal in response to the fluid flow in the bypass fluid channel, and
      a microcontroller connected with the fluid flow sensor for calculating the fluid flow from the signal generated by the flow sensor;

further comprising a communication means for the exchange of data related to the fluid flow generated by the spirometer; and a first air quality measurement device comprising communication means adapted for data exchange with the portable electronic spirometer and/or with a separate computing unit, and equipped with one or more air quality sensors for determining the air quality at the location of the first air quality measurement device, wherein the first air quality measurement device further serves as a charging dock for at least the portable electronic spirometer.

44. The system of claim 43, wherein the charging is a Near Field Communication (NFC) charging dock.

45. The system of claim 43, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

46. A system comprising:
a portable electronic spirometer comprising:
(a) a tubular mouthpiece with
a proximal opening for insertion into the mouth of a user,
a distal opening,
a main fluid channel extending between the proximal opening and the distal opening,
a first lateral opening,
a second lateral opening positioned at a longitudinal distance to the first lateral opening, and
a flow restrictor positioned in the main fluid channel between the first and the second lateral opening; and
(b) a main body with
a first fluid opening connectible with the first lateral opening of the mouthpiece,
a second fluid opening connectible with the second lateral opening of the mouthpiece,
a bypass fluid channel extending between the first and the second fluid opening,
a MEMS-based thermal fluid flow sensor positioned at the bypass fluid channel for generating a signal in response to the fluid flow in the bypass fluid channel, and
a microcontroller connected with the fluid flow sensor for calculating the fluid flow from the signal generated by the flow sensor;
further comprising a communication means for the exchange of data related to the fluid flow generated by the spirometer; and
a first air quality measurement device comprising communication means adapted for data exchange with the portable electronic spirometer and/or with a separate computing unit, and equipped with one or more air quality sensors for determining the air quality at the location of the first air quality measurement device;
wherein the system further comprises a second air quality measurement device adapted for data exchange with the portable electronic spirometer and/or with a separate computing unit, and equipped with one or more air quality sensors in order to determine the air quality at the location of the second air quality measurement device.

47. The system of claim 46, wherein the separate computing unit also collects and analyses the data obtained from the second air quality measurement device.

48. The system of claim 46, wherein the one or more air quality sensors of the first air quality measurement device, and the one or more air quality sensors of the second air quality measurement device, are each independently selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

49. A system comprising:
A portable electronic spirometer comprising:
(a) a tubular mouthpiece with
a proximal opening for insertion into the mouth of a user,
a distal opening,
a main fluid channel extending between the proximal opening and the distal opening,
a first lateral opening,
a second lateral opening positioned at a longitudinal distance to the first lateral opening, and
a flow restrictor positioned in the main fluid channel between the first and the second lateral opening; and
(b) a main body with
a first fluid opening connectible with the first lateral opening of the mouthpiece,
a second fluid opening connectible with the second lateral opening of the mouthpiece,
a bypass fluid channel extending between the first and the second fluid opening,
a MEMS-based thermal fluid flow sensor positioned at the bypass fluid channel for generating a signal in response to the fluid flow in the bypass fluid channel, and
a microcontroller connected with the fluid flow sensor for calculating the fluid flow from the signal generated by the flow sensor;
further comprising a communication means for the exchange of data related to the fluid flow generated by the spirometer; and
a first air quality measurement device comprising communication means adapted for data exchange with the portable electronic spirometer and/or with a separate computing unit, and equipped with one or more air quality sensors for determining the air quality at the location of the first air quality measurement device;
further comprising a separate computing unit adapted to collect and analyse at least the data obtained from the spirometer and from the first air quality measurement device;
wherein the separate computing unit further allows for the geolocalisation of at least the air quality data obtained from the first air quality measurement device.

50. The system of claim 49, wherein the separate computing unit further allows for the geolocalisation of at least the air quality data obtained from the first air quality measurement device and of the air quality data obtained from the second air quality measurement device.

51. The system of claim 49, wherein the one or more air quality sensors are selected from the group consisting of humidity sensors, temperature sensors, atmospheric pressure sensors, MOS-type gas sensors (metal-oxide-semiconductor), airborne-particles sensors, pollen sensors, ozone ($O_3$) sensors, nitrogen dioxide ($NO_2$) sensors, sulfur dioxide ($SO_2$) sensors and carbon monoxide (CO) sensors.

52. A method for measuring a health parameter of a human subject selected from:
(a) a forced vital capacity,
(b) a forced expiratory volume,
(c) a peak expiratory flow,
(d) a forced expiratory flow (FEF), (e) a maximum voluntary ventilation (MVV),
(f) a mean expiratory flow,
(g) a slow vital capacity (SVC),
(h) a functional residual capacity (FRC),
(i) an expiratory reserve volume (ERV),
(j) a maximum speed of expiration,
(k) a forced inspiratory volume (FIV),
(l) a forced inspiratory vital capacity (FIVC),
(m) a peak inspiratory flow (PIF), or any combination of these, the method comprising a step of the human subject performing a breathing manoeuvre through a portable electronic spirometer comprising:

(a) a tubular mouthpiece with
   a proximal opening for insertion into the mouth of a user,
   a distal opening,
   a main fluid channel extending between the proximal opening and the distal opening,
   a first lateral opening,
   a second lateral opening positioned at a longitudinal distance to the first lateral opening, and
   a flow restrictor positioned in the main fluid channel between the first and the second lateral opening; and (b) a main body with
   a first fluid opening connectible with the first lateral opening of the mouthpiece,
   a second fluid opening connectible with the second lateral opening of the mouthpiece,
   a bypass fluid channel extending between the first and the second fluid opening,
   a MEMS-based thermal fluid flow sensor positioned at the bypass fluid channel for generating a signal in response to the fluid flow in the bypass fluid channel, and
   a microcontroller connected with the fluid flow sensor for calculating the fluid flow from the signal generated by the flow sensor;

wherein the one or more health parameter obtained with the spirometer is correlated with air quality data, and optionally geolocalisation data.

* * * * *